US006204049B1

(12) United States Patent
Bennett et al.

(10) Patent No.: US 6,204,049 B1
(45) Date of Patent: Mar. 20, 2001

(54) FUNGAL COMPOSITIONS FOR BIOREMEDIATION

(75) Inventors: Joan Wennstrom Bennett; Adele Marie Childress, both of New Orleans; Kenneth George Wunch, Metaire; William Joseph Connick, Jr., New Orleans, all of LA (US)

(73) Assignees: The United States of America as represented by the Secretary of Agriculture, Washington, DC (US); The Administrators of Tulane Educational Fund, New Orleans, LA (US)

( * ) Notice: Subject to any disclaimer, the term of this patent is extended or adjusted under 35 U.S.C. 154(b) by 0 days.

(21) Appl. No.: 08/599,260

(22) Filed: Feb. 9, 1996

(51) Int. Cl.$^7$ .............................. C12N 1/14; C12S 13/00

(52) U.S. Cl. ................. 435/254.1; 435/262; 435/262.5; 424/490

(58) Field of Search ................................ 435/262, 262.5, 435/259.1; 424/490

(56) References Cited

U.S. PATENT DOCUMENTS

| | | | |
|---|---|---|---|
| 3,649,239 | 3/1972 | Mitchell | 71/23 |
| 4,178,389 | * 12/1979 | Pilla | 426/11 |
| 4,400,391 | 8/1983 | Connick | 71/88 |
| 4,401,456 | 8/1983 | Connick | 424/304 |
| 4,668,512 | 5/1987 | Lewis et al. | 424/93 |
| 4,718,935 | 1/1988 | Walker et al. | 71/79 |
| 4,724,147 | 2/1988 | Marois et al. | 424/93 |
| 5,085,998 | 2/1992 | Lebron et al. | 435/262 |
| 5,091,089 | * 2/1992 | Shen et al. | 210/917 |
| 5,278,058 | 1/1994 | Call | 435/183 |
| 5,286,495 | * 2/1994 | Batich et al. | 424/490 |
| 5,342,779 | 8/1994 | Matsumura et al. | 435/262.5 |
| 5,631,160 | * 5/1997 | Bruso | 435/262.5 |

FOREIGN PATENT DOCUMENTS 0 646 642 A2    4/1995   (EP) .

OTHER PUBLICATIONS

Sack, et al. J. Basic Microbiol. vol. 33(4): pp. 269–277, 1993.*
Wunch et al., Abstracts of the general meeting of the American Society for Microbiology (1994), 94(0):468, Q–455.*
Natarajan et al., South Indian Agaricales XXI, Kavaka (1986(1988)), 14(1–2): 47–60.*
Bennett et al., "Comparison of alginate and "pesta" for formulation of *Phanerochaete chrysosporium*," *Biotechnol. Techniques* 10:7–12 (Jan. 1996).

Bumpus, "Microbial degradation of environmentally persistent organopollutants: recent progress and future promise," In *Biotechnology for Aerospace Applications*, eds. Obringer & Tillinghast, pp 59–84, in *Advances in Applied Biotechnology Series*, vol. 3, Portfolio Publishing Co., Woodlans, Texas (presented Mar. 1989).
Trevors et al., "Use of alginate and other carriers for encapsulation of microbial cells for use in soil," *Microbial Releases* 1:61–69 (1992).
Alexander, "Biodegradation of chemicals of environmental concern," *Science* 211:132–138 (1981).
Atlas et al., "Bioremediation of petroleum pollutants. Diversity and environmental aspects of hydrocarbon degradation," *Bioscience* 45:332–339 (May 1995).
Aust, "Degradation of environmental pollutants by *Phanerochaete chrysosporium*," *Microbial Ecology* 20:197–209 (1990).
Barr & Aust, "Mechanisms white rot fungi use to degrade pollutants," *Environmental Science Technology* 28:78A–87A (1994).
Bashan, "Alginate beads as synthetic inoculant carriers for slow release of bacteria that affect plant growth," *Appl. Environ. Microbiol.* 51:1089–1098 (1986).
Bumpus et al., "Oxidation of persistent environmental pollutants by a white rot fungus," *Science* 220:1434–1438 (1985).
Bumpus & Aust, "Mineralization of recalcitrant environmental pollutants by a white rot fungus," Proceedings of the National Conference on Hazardous Wastes and Hazardous Materials, pp. 146–151 (1987).
Cerniglia & Gibson, "Oxidation of benzo[a]pyrene by the filamentous fungus *Cunninghamella elegans*," *J. Biol. Chem.* 254:12174–12180 (1979).
Cerniglia et al., "Fungal oxidation of benzo[a]pyrene. Formation of (–)–trans–7,8–dihydroxy–7,8–dihydrobenzo(a)pyrene by *Cunninghamella elegans*," *Biochem. Biophys. Res. Commun.* 94:226–232 (1980).
Cerniglia & Gibson, "Fungal oxidation of (+) 9,10–dihydroxy–9,10–dihydrobenzo[a]pyrene. Formation of diastereomeric benzo[a]pyrene 9,10–diol 7,8–epoxides," *Proc. Natl. Acad. Sci. USA* 77:4554–4558 (1980).
Cerniglia et al., "Glucuronide and sulfate conjugation in the fungal metabolism of aromatic hydrocarbons," *Appl. Environ. Microbiol.* 43:1070–1075 (1982).

(List continued on next page.)

Primary Examiner—Lorraine Spector
Assistant Examiner—Claire M. Kaufman
(74) Attorney, Agent, or Firm—Michael L. Murray

(57) ABSTRACT

Compositions and methods for bioremediation of sites contaminated with chemical pollutants, wherein survival and colonization of a polluted medium by a fungal microorganism having the capacity to degrade a chemical pollutant is enhanced; and microorganisms having the capacity to degrade one or more priority pollutants.

2 Claims, 6 Drawing Sheets

OTHER PUBLICATIONS

Figure 1A:
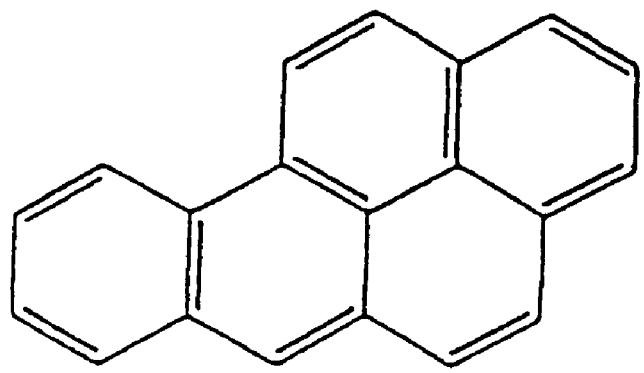

Cerniglia, "Microbial metabolism of polycyclic aromatic hydrocarbons," *Adv. Appl. Microbiol.* 30:31–71 (1984).

Cerniglia, et al., "Fungal metabolism of aromatic hydrocarbons" in *Microbial Degradation of Natural Products*, Ed. G. Winkelman, VCH Press, Weinheim (1992) pp. 193–217.

Connell & Miller, "Chemistry & ecotoxicology of pollution," pp. 1–48 & 231–247, John Wiley & Sons, Inc., New York, NY. (1984).

Connick, "Formulation of living biological control agents with alginate," in B. Cross & H.B. Scher (eds.) *Pesticide Formulations: Innovations & Developments*, American Chemical Society, Washington, D.C., pp. 241–250 (1988).

Connick et al., "Formulation of mycoherbicides using a pasta–like process," *Biological Control*, 1:281–287 (1991).

Daigle & Cotty, "Formulating atoxigenic *Aspergillus flavus* for field release," *Biocontrol Science & Technology* 5:174–184 (1995; after Feb. 1995).

Datta & Samanta, "Effect of inducers on metabolism of benzo[a]pyrene in vivo and in vitro: analysis by high pressure liquid chromatography," *Biochem. Biophys. Res. Comm.* 155:493–502, (1988).

Fernando & Aust, "Biodegradation of toxic chemicals by white rot fungi," in *Biological degradation and bioremediation of toxic chemicals*, pp. 386–400, Ed. G. Chaudry, Dioscorides Press, Portland, OR (1994).

Field et al., "Biodegradation of polycyclic aromatic hydrocarbons by new isolates of white rot fungi,"*Appl. Environ. Microbiol.* 58:2219–2226 (1992).

Field et al., "Screening for lignolytic fungi applicable to the biodegradation of xenobiotics," *Trends Biotechnol.* 11:44–48 (1993).

Fravel et al., "Encapsulation of potential biocontrol agents in an alginate–clay matrix," *Phytopathology* 75:774–777 (1985).

Gibson & Subramanian, "Microbial degradation of aromatic hydrocarbons," in *Microbial Degradation of Organic Compounds*, Ed. T. Gibson, Marcel Dekker, Inc., New York, (1984) pp. 181–252.

Haemmerli et al., "Oxidation of benzo[a]pyrene by extracellular ligninase of *Phanerochaete chrysosporium*," *J. Biol. Chem.* 261:6900–6903 (1986).

Hale et al., "Biodegradation of chlorinated homocyclic and heterocyclic compounds in anaerobic environments," in *Biological degradation and bioremediation of toxic chemicals*, Ed. G. Chaudry, Dioscorides Press, Portland, OR, (1994).

Heitkamp et al., "Polycyclic aromatic hydrocarbon degradation by a *Mycobacterium sp.*in microcosms containing sediment and water from a pristine ecosystem," *Appl. Environ. Microbiol.* 55:1968–1973 (1989).

Johnson & Larsen, "The distribution of polycyclic aromatic hydrocarbons in the surficial sediments of Penobscot Bay (Maine, USA) in relation to possible sources and to other sites worldwide," *Mar. Environ. Res.* 15:1–16 (1985).

Kappeli, "Cytochromes P–450 of yeasts," *Microbiol. Rev.* 50:244–258 (1986).

Lestan & Lamar, "Development of fungal inocula for bioaugmentation of contaminated soils," *Appl. Environ. Microbiol.* 62:2045–2052 (Jun. 1996).

Levinson et al., "Hazardous waste cleanup and treatment with encapsulated or entrapped microorganisms," in *Biological degradation and bioremediation of toxic chemicals*, Ed. G. Chaudry, Dioscorides Press, Portland, OR, (1994), pp. 455–469.

Livernoche et al., "Decolorization of a Kraft mill effluent with fungal mycelium immobilized in calcium alginate gel," *Biotechnol. Lett.* 3:701–706 (1981).

Morgan & Watkinson, "Hydrocarbon degradation in soils & methods for soil biotreatment," *CRC Critical Reviews in Biotechnology* 8:305–333 (1989).

Morgan et al., "Comparison of abilities of white rot fungi to mineralize selected xenobiotic compounds," *Appl. Microbiol. Biotechnol.* 34:693–696 (1991).

Mugnier & Jung, "Survival of bacteria and fungi in relation to water activity and solvent properties of water in biopolymer gels," *Appl. Environ. Microbiol.* 50:108–114 (1985).

Phillips, "Fifty years of benzo[a]pyrene," *Science* 303:468–472 (1983).

Providenti et al., "Selected factors limiting the microbial degradation of recalcitrant compounds," *J. Indust. Microbiol.* 12:379–395 (1993).

Riser–Roberts, "Bioremediation of petroleum contaminated sites," pp. 1–34, *CRC Press*, Boca Raton, FL (1992).

Sanglard et al., "Role of extracellular ligninases in the biodegradation of benzo[a]pyrene by *Phanerochaete chrysosporium,"* Enzyme Microbiol. Technol.* 8:209–211 (1986).

Smidsrod & Skjak–Braek, "Alginate as immobilization matrix for cells," *Trends Biotechnol.* 8:71–81 (1990).

Sutherland et al., "Metabolism of phenanthrene by *Phanerochaete chrysosporium*," *Appl. Environ. Microbiol.* 57:3310–3316 (1991).

Sutherland, "Detoxification of polycyclic aromatic hydrocarbons by fungi," *J. Industrial Microbiol.* 9:53–62 (1992).

Thakker, et al., "Polycyclic aromatic hydrocarbons: Metabolic activation to ultimate carcinogens" in *Bioactivation of Foreign Compounds*, Ed. M.W. Anders, Academic Press, Orlando, FL (1985) pp. 177–242.

van Elsas & Heijnen, "Methods for the introduction of bacteria in to the soil: A review," *Biol. Fertil. Soils* 10:127–133 (1990).

van Schraven, "Some factors affecting growth & survival of Rhizobium spp. in soil–peat cultures," *Plant & Soil* 32:113–130 (1970).

Walker et al. "Sodium alginate for production and formation of mycoherbicides," *Weed Science* 31:333–338 (1983).

Weir et al., "Nutrient–enhanced survival of and phenanthrene mineralization by alginate–encapsulated and free *Pseudomonas sp.* UG14Lr cells in creosote–contaminated soil slurries," *Appl. Microbiol. Biotechnol.* 43:946–951 (Jun. 1995).

Weir et al., "Effect of alginate–encapsulation and selected disinfectants on survival of and phenanthrene mineralization by *Pseudomonas sp.* UG14Lr in creosote–contaminated soil," *J. Indust. Microbiol.* 16:62–67 (1996).

\* cited by examiner

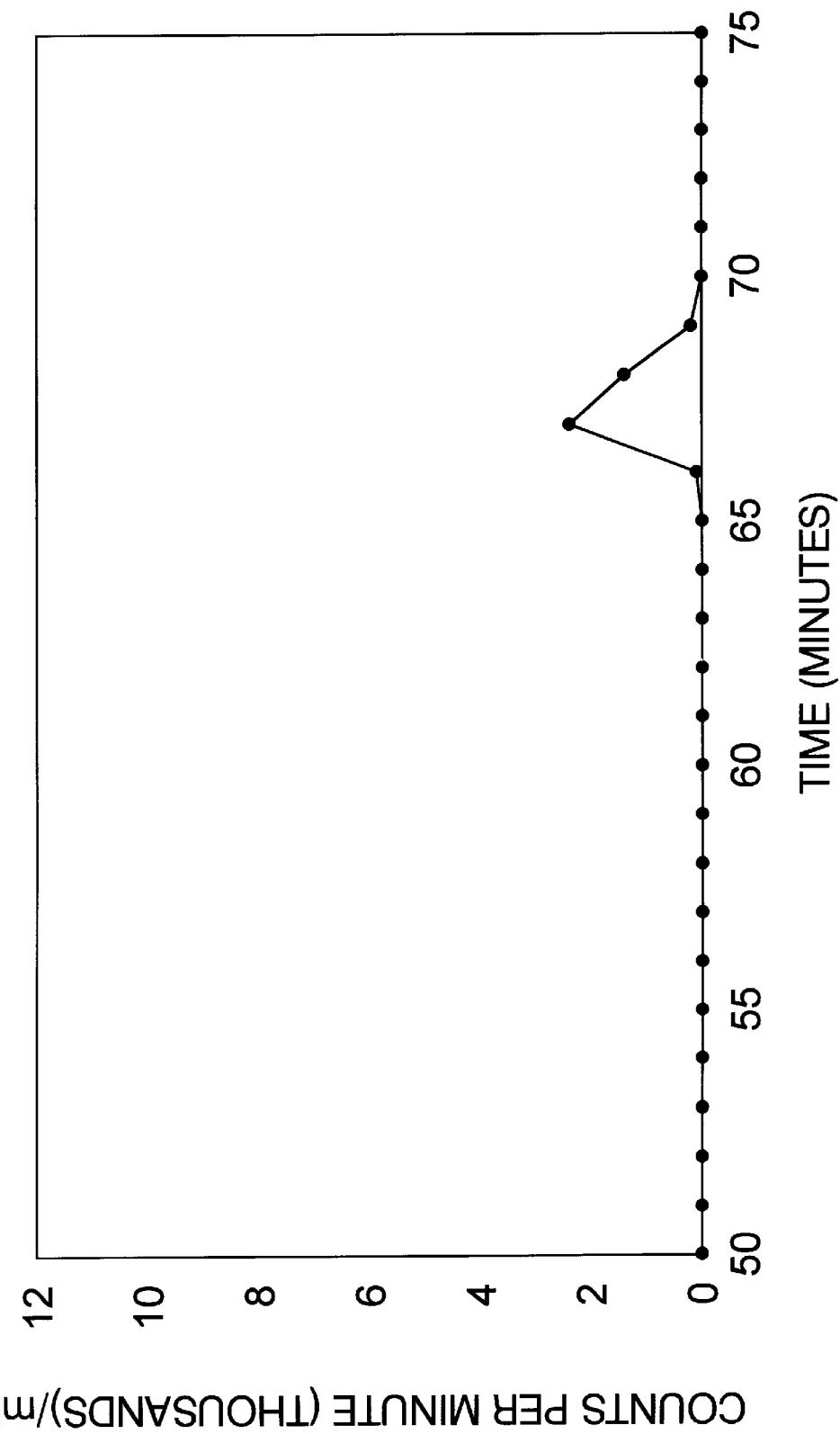

FUNGAL COMPOSITIONS FOR BIOREMEDIATION

This invention was made with Government support by Grant No. DAAH04-93-6-0292 awarded by the Department of Defense. The Government may have certain rights in the invention.

BACKGROUND OF THE INVENTION

1. Field of the Invention

This invention relates generally to the formulation of microorganisms for delivery of viable inoculum of the microorganisms to an environment. This invention also relates generally to the formulation of microorganisms for delivery of viable inoculum of the microorganisms to an environment having an indigenous microflora and to a polluted environment or site. Methods of formulating viable inoculum of microorganisms for delivery of the microorganisms to a polluted environment or site, and a method for remediation of a polluted environment or site are presented, in which a suitable microorganism having the capacity to decompose a pollutant, is applied to the site in combination with a suitable carrier for the microorganism.

The invention also relates to compositions for remediating an environment or site which has been contaminated with a chemical pollutant, and to methods for delivering microorganisms in combination with a carrier for the microorganisms to an environment or site which has been contaminated with a chemical pollutant and which is subject to bioremediation. Methods are presented for delivering nutrients in combination with a carrier for the nutrients to an environment or site which has been contaminated with a chemical pollutant and which is subject to bioremediation, as are methods for delivering nutrients in combination with a microorganism and a carrier to an environment or site which has been contaminated with a chemical pollutant and which is subject to bioremediation.

Embodiments of the invention are presented relating to the biodegradation of benzo[a]pyrene, and to the fungus *Marasmiellus troyanus*. In particular, *Marasmiellus troyanus* isolate no. 216-1867 is presented, and compositions comprising *M. troyanus* isolate no. 216-1867 in combination with a carrier are presented. Yet further, the invention relates to the degradation of benzo[a]pyrene by *M. troyanus*, and the mineralization of benzo[a]pyrene by *M. troyanus*. A process for bioremediation of polluted media contaminated with benzo[a]pyrene is also shown.

2. Background of the Related Art

Chemical pollution of various media (e.g. soil, water) is a common problem worldwide which has a major economic impact at the local, national, and global levels. The remediation of sites polluted or contaminated with toxic chemicals or hazardous wastes using existing technologies is generally extremely costly, laborious and time-consuming. For example, in the U.S., Congress established a multibillion dollar fund (the Superfund) under the Comprehensive Environmental Response, Compensation, and Liability Act of 1980, 1986 and 1990 (commonly known as the Superfund Act). The fund was established to pay for cleanup of polluted sites such as hazardous and municipal waste dumps, contaminated factories and mines, and leaking underground fuel storage tanks. During the eleven years between its inception and 1991, 30,000 potential Superfund sites were surveyed. The time required for cleanup of a Superfund site by the EPA has been as long as 10 years. Remediation efforts at hazardous waste sites have been partially effective 54% of the time and completely effective only 16% of the time (Riser-Roberts, E., (1992) *"Bioremediation of Petroleum Contaminated Sites,"* pp. 1–34, CRC Press, Boca Raton, Fla.). Currently, additional sites of chemical pollution are being discovered and new sites of pollution are being created worldwide.

Pollution of the soil with toxic chemicals creates hazards to the health of humans and other organisms, and also renders the site useless for most purposes. In addition, pollutants in the soil can be leached into underlying aquifers leading to groundwater contamination. In the U.S., groundwater is used as a source of drinking water by about 120 million people, and is also widely used to irrigate food crops.

Improved technologies for remediation of polluted soil and water are urgently needed. Traditional methods for cleanup of contaminated soil has generally involved excavation of the soil, followed by treatment or containment. Currently used techniques for remediating polluted soils include, for example, the physical removal of volatile materials by aspiration (vacuum extraction) and the incineration of contaminated soil. Because of the large volumes of soil usually involved, physicochemical methods such as those exemplified above may be prohibitively expensive. An alternative approach to cleaning up sites of chemical pollution is bioremediation, in which a biological organism is used as an agent for converting the chemical pollutant to less toxic or nontoxic compounds. For example, various microorganisms have been found to detoxify a number of toxic chemical pollutants (see, for example, G. Chaudry (Ed.) *"Biological degradation & bioremediation of toxic chemicals,"* Dioscorides Press, Portland, Oreg., 1984). Biodegradation or detoxification of chemical pollutants is normally the result of one or more enzymatic reactions, including oxidation, reduction, hydrolysis, and conjugation (see, for example, D. W. Connell, & G. J. Miller, (1984) *"Chemistry & Ecotoxicology of Pollution,"* pp. 1–48 & 231–247, John Wiley & Sons, Inc., New York, N.Y.).

One factor limiting the efficacy of prior art bioremediation processes is the tendency of microorganisms to lose viability and decline in number following their introduction to the remediation site. It has been demonstrated by numerous field trials that, in general, microorganisms released into the soil tend not to spread from the point of application, and further that their numbers tend to decline over time (see, for example, J. D. van Elsas, & C. E. Heijnen, "Methods for the introduction of bacteria into the soil: A review," *Biol. Fertil. Soils,* 10:127–133, 1990). Factors militating against the propagation and survival of microorganisms introduced into soils include: competition with other organisms for nutrients, water and space; parasitism, antibiosis and predation by other organisms; and unfavorable physicochemical parameters of the soil milieu, including sub-optimal pH, water and oxygen concentrations. In the case of polluted soils, problems associated with survival and propagation of microorganisms introduced into such soil may be exacerbated by the presence of toxic pollutants at concentrations which are inimical to microbial growth.

In an attempt to prolong the survivability of microorganisms introduced into soil, some prior art remediation techniques have incorporated increased aeration or the large-scale application of nutrients to the soil. However, this approach is expensive and, in addition, nutrients added to the soil en masse are immediately available to the soil microflora as a whole, and consequently are prone to rapid depletion.

Another approach to increasing survivability of microorganisms introduced into soil, or other environments, is to combine the microorganisms with various carrier materials. Such carriers include a variety of organic and inorganic materials, including silica, mineral oil, peat, and various gels (see, for example, D. A. Van Schreven, "Some factors affecting growth and survival of Rhizobium spp. in soil-peat cultures," *Plant & Soil*, 32:113–130, 1970; Fravel, D. R., et al., "Encapsulation of potential biocontrol agents in an alginate-clay matrix," *Phytopathology*, 75:774–777, 1985; W. J. Connick, Jr., "Formulation of living biological control agents with alginate," in B. Cross & H. B. Scher (eds.) *"Pesticide formulations: innovations & developments,"* American Chemical Society, Washington, D.C., pp. 241–250, 1988).

Apart from a carrier in combination with a microorganism serving as a vehicle for the microorganism, in some cases the particular combination of a suitable carrier material with a certain microorganism provides the added advantage of preserving the microorganism, thereby allowing for storage of the microorganism in a viable state (see, for example, D. J. Daigle & P. J. Cotty, "Formulating atoxigenic *Aspergillus flavus* for field release," *Biocontrol Science & Technology*, 5:174–184, 1995; D. R. Fravel, et al., "Encapsulation of potential biocontrol agents in an alginate-clay matrix," *Phytopathology*, 75:774–777, 1985; W. J. Connick, Jr., "Formulation of living biological control agents with alginate," in B. Cross & H. B. Scher (eds.) *"Pesticide formulations: innovations & developments,"* American Chemical Society, Washington, D.C., pp. 241–250, 1988).

As mentioned above, in numerous field trials microorganisms have been released into the soil but their survival has been limited and their effectiveness poor due to the complex interactions and harsh conditions within the soil environment (J. D. van Elsas, & C. E. Heijnen, "Methods for the introduction of bacteria into the soil: A review," *Biol. Fertil. Soils*, 10:127–133, 1990). Techniques for in situ bioremediation of polluted soil can profit from lessons learned in nitrification, biocontrol, and other areas of applied microbiology in which living microorganisms are introduced into the environment. For example, to address the problems of lack of survival and effectiveness, microorganisms have been formulated with various carriers and encapsulating agents, and the formulations applied to the particular environment with varying results. One such carrier or encapsulating agent that has been used to encapsulate various fungi is alginate, a naturally occurring β-1,4-linked copolymer of α-L-glucuronate and β-D-mannuronate. Alginate gel is non-toxic and biodegradable, making alginate gel beads well-suited as vehicles for the release of microorganisms, nutrients, etc., into the environment.

Livernoche et al., describe the use of alginate-encapsulated white rot fungus, *Coriolus versicolor*, to decolorize kraft mill effluents containing lignin (D. Livernoche, et al., "Decolorization of a Kraft mill effluent with fungal mycelium immobilized in calcium alginate gel," *Biotechnol. Lett.* 3:701–706, 1981). Alginate-encapsulated *C. versicolor* has also been used as mushroom spawn.

Various fungi have been combined with carrier materials for application to plant surfaces, soil, or soil surfaces for the purposes of biological pest control. For example, U.S. Pat. No. 4,718,935 to Walker et al. discloses the encapsulation of mycoherbicidal fungi in alginate gel pellets as a form of mass-produced inoculum for the control of weeds.

U.S. Pat. No. 4,724,147 to Marois et al. discloses the encapsulation of fungi in alginate pellets as inoculum for the control of soil-borne plant diseases in agriculture.

U.S. Pat. No. 4,668,512 to Lewis et al. discloses the formulation of fungi with wheat bran to form alginate gel pellets, for the control of soilborne plant pathogens, wherein the wheat bran provides a nutrient source for the fungus.

None of the patents cited above, alone or in combination, teaches formulation of microorganisms having the capacity to degrade chemical pollutants, or the use of such organisms for bioremediation. Furthermore, the use of wheat bran in a fungal inoculum formulation, as taught by the process of Lewis et al., is not suitable for some fungi. Thus, we have found that the white rot fungus *Phanerochaete chrysosporium* formulated with wheat bran did not yield growth of the fungus after the wheat bran-formulated fungus was plated on a nutrient medium. Moreover, our subsequent studies have demonstrated that wheat bran, as well as other wheat products including purified wheat gluten, actually caused inhibition of growth of *P. chrysosporium* growing from alginate gel beads formulated without wheat bran. On the other hand, inhibition of growth of *P. chrysosporium* or other fungi has not been observed when sawdust, corncob grits, Pyrax clay or any other non-wheat based materials were used to formulate fungal inoculum according to the instant invention.

Connick, Jr. discloses in U.S. Pat. Nos. 4,401,456 and 4,400,391 processes for the incorporation of biocidal chemical compounds, such as insecticides and herbicides, into alginate gels. Certain biocidal compounds, e.g. some pesticides, are known as environmental pollutants and as such are potentially subject to various bioremediation techniques, including the techniques disclosed herein. U.S. Pat. Nos. 4,401,456 and 4,400,391 do not teach the encapsulation of fungi or other organisms.

Mitchell, in U.S. Pat. No. 3,649,239 teaches formulations of fertilizers, either as solutions or emulsions, in combination with alginate for the purpose of slow release of fertilizer to soil. U.S. Pat. No. 3,649,239 does not teach formulation of microbial inoculum, nor encapsulation of fungi or of other organisms.

U.S. Pat. No. 5,085,998 to Lebron et al. discloses the degradation of 2,4,6-trinitrotoluene (TNT) by contacting either a liquid culture or a soil-corncob culture of *P. chrysosporium* with a quantity of TNT. Lebron et al. do not disclose encapsulation of fungi within alginate, nor the degradation of polyaromatic hydrocarbons or other pollutants other than TNT.

U.S. Pat. No. No. 5,278,058 to Call discloses the production of lignolytical (lignolytic) enzymes by *Phanerochaete chrysosporium* cultured in a fermentation vessel which is agitated by rotating and slewing movements of the vessel. U.S. Pat. No. 5,278,058 does not disclose the encapsulation of fungi in a carrier, vehicle or gelling agent.

Matsumura et al., U.S. Pat. No. 5,342,779 discloses the use of *Phanerochaete chrysosporium* for the degradation of halogenated organic compounds in a polluted medium by contacting the medium with the fungus, and simultaneously exposing the medium to ultraviolet radiation. Matsumura et al. do not teach the encapsulation of a microorganism with a carrier, vehicle or gelling agent.

Komatsu et al., EP publication No. 0646642 A2, discloses a microorganism (bacteria) in combination with a carrier and an inducer of a degradative enzyme, in which the microorganism is adsorbed on a surface of a carrier or on a surface of a water-absorbent polymer, and the microorganism and the carrier form an integral unit in that the microorganism remains in permanent association with the carrier. Thus, Komatsu et al. do not teach encapsulation of microorganisms with a carrier wherein the microorganism grows from the carrier and propagates itself within the medium in the absence of the carrier.

None of the patents or publications cited above teach the application of a microorganism formulated as an alginate bead to contaminated soil or to any other medium having toxic chemical pollutants therein, wherein the organism can remain viable within the alginate bead carrier for an extended period of time following application to the polluted medium; and the organism may grow away from the alginate bead carrier into the surrounding polluted medium and propagate itself, in the absence of the carrier, within the polluted medium; thereby the organism effectively colonizes the polluted medium into which the alginate bead formulation of the organism was introduced. Indeed, the ability to maintain a viable culture within the soil environment for a long enough duration, and in proximity to the target pollutant(s), has been the limiting factor in most bioremediation applications to date.

The degradation of toxic pollutants by many microorganisms, and particularly by bacteria, requires the pollutant to be not only in contact with or proximate to the microorganism, but also to be taken up by the cell where it can interact with intracellular degradative enzyme(s). White rot fungi, on the other hand, can perform this remedial function by the release of extracellular enzymes, such as ligninases. The mechanisms of enzymic degradation exhibited by many lignicolous microorganisms are non-specific and non-stereo selective, thereby increasing the metabolic versatility of such organisms and making them highly advantageous for bioremediation of sites contaminated with various pollutants. Likewise the considerable latitude in formulating degradative organisms as disclosed herein, increases the likelihood that any given degradative microorganism will have the ability to survive within, and colonize, a particular polluted medium subject to remediation.

Although to date, the majority of microorganisms used for bioremediation have been bacteria (prokaryotes), fungi (eukaryotes) are also potentially valuable in this regard. For example, in vitro laboratory studies with the lignolytic white rot fungi, such as *Phanerochaete chrysosporium*, have shown the ability of these fungi to degrade a range of toxic compounds including polychlorinated biphenyls (PCBs), chlorinated pesticides, polyaromatic hydrocarbons, such as benzo[a]pyrene, pyrene, phenanthrene, fluorene, and nitroaromatic compounds (e.g. trinitrotoluene, TNT). D. P. Barr & S. D. Aust "Mechanisms white rot fungi use to degrade pollutants," *Environmental Science Technology* 28:78A–87A, 1994; J. A. Bumpus et al. "Oxidation of persistent environmental pollutants by a white rot fungus," *Science* 220:1434–1438, 1985. The ability of Phanerochaete spp. to degrade a range of structurally unrelated compounds has been ascribed largely to their lignolytic metabolic activity (S. D. Aust "Degradation of environmental pollutants by. *Phanerochaete chrysosporium*," Microbial Ecology, 20:197–209, 1990).

Despite the ability of *P. chrysosporium* and other lignolytic fungi to degrade numerous toxic pollutants, there has been little commercial success in applying these organisms to bioremediation. A major factor limiting the use of *P. chrysosporium* in bioremediation is the difficulty of introducing inoculum of the fungus to a contaminated medium in a manner that enables the fungus to grow and propagate within the medium. However, *P. chrysosporium* is not alone in this regard. On the contrary, it is normally problematic to establish recently-introduced microorganisms in a medium having an established indigenous microflora. The compositions and methods of the instant invention are designed to overcome the difficulty of establishing an introduced microorganism in such a medium, and to allow the successful use of a number of potentially valuable degradative organisms in bioremediation.

Figure 1B:
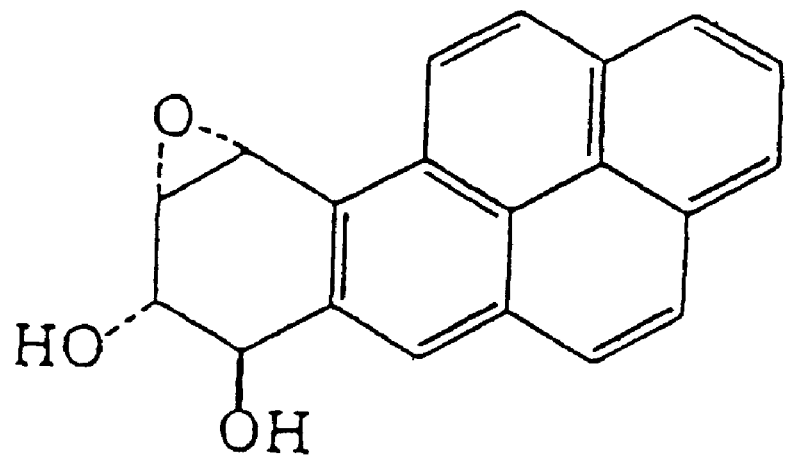

A common chemical pollutant of soil which has been reported from industrial sites worldwide is benzo[a]pyrene (see, for example, A. C. Johnson & D. Larsen "The distribution of polycyclic aromatic hydrocarbons in the surficial sediments of Penobscot Bay (Me., USA) in relation to possible sources and to other sites worldwide," *Mar. Environ. Res.*, 15:1–16, 1985). Benzo[a]pyrene is one of a large number of polybenzenoid hydrocarbons. The structure of benzo[a]pyrene is depicted in FIG. 1A. Benzo[a]pyrene is one of the most potent known carcinogens within the polycyclic aromatic hydrocarbons. The actual carcinogen is a diol epoxide metabolite of benzo[a]pyrene resulting from enzymatic oxidation of benzo[a]pyrene which has entered the body. The diol epoxide (FIG. 1B) alkylates DNA leading to mutations. The accumulation of benzo[a]pyrene is therefore a threat to the environment and public health.

Benzo[a]pyrene occurs in crude petroleum, in petroleum products such as coal tar, and in fossil fuel by-products such as soot. Most accumulations of benzo[a]pyrene in the environment result, directly or indirectly, from the incomplete combustion of fossil fuels. Benzo[a]pyrene is extremely persistent in the environment due to its low solubility, chemical stability and resistance to degradation by most organisms. Indeed, many hydrocarbon-degrading bacteria are unable to break apart the fused benzene rings of benzo [a]pyrene. Further, those bacteria which have the ability to degrade benzo[a]pyrene have proved difficult to establish at contaminated sites.

SUMMARY OF THE INVENTION

It is an object of the instant invention to provide a method of preparing inoculum of a microorganism for introduction into soil which is contaminated with a chemical pollutant.

It is a further object of the instant invention to provide a method of preparing inoculum of a microorganism, having the capacity to degrade a chemical pollutant, for introduction of the microorganism into soil contaminated with the chemical pollutant.

It is a further object of the instant invention to provide a method of preparing inoculum of a microorganism for introduction into soil, wherein the microorganism retains viability within the soil.

It is a further object of the instant invention to provide a method of preparing inoculum of a microorganism in combination with a carrier material wherein the microorganism retains viability for an extended period of time in the presence of a limited supply of nutrients.

It is a further object of the instant invention to provide a method of preparing inoculum of a microorganism in combination with a carrier material wherein the microorganism remains dormant for an extended period of time in the presence of a supply of nutrients.

It is a further object of the instant invention to provide a method of preparing inoculum of a microorganism in combination with a carrier material wherein the carrier material comprises a non-toxic naturally-occurring water-absorbent material.

It is a further object of the instant invention to provide a method of preparing inoculum of a microorganism in combination with a carrier material wherein the microorganism is encapsulated within the carrier material.

It is a further object of the instant invention to provide a method of preparing inoculum of a microorganism in combination with a carrier material wherein the microorganism may release itself from the carrier material and propagate itself in the absence of carrier material in a polluted medium.

It is a further object of the instant invention to provide a method of preparing inoculum of a Marasmiellus sp. in combination with a carrier.

It is a further object of the invention to provide a method of preparing inoculum of a fungus for introduction into a polluted medium, wherein the fungus releases an enzyme into the polluted medium.

It is a further object of the instant invention to provide a method of preparing inoculum of a Marasmiellus sp. in combination with a carrier material wherein the Marasmiellus sp. has the capacity to degrade a polycyclic aromatic hydrocarbon.

It is a further object of the instant invention to provide a method of preparing inoculum of a Marasmiellus sp. in combination with a carrier material wherein the Marasmiellus sp. has the capacity to mineralize benzo[a]pyrene.

It is a further object of the instant invention to provide a method of preparing inoculum of a Marasmiellus sp. in combination with a carrier material wherein the Marasmiellus sp. may release itself from the carrier material and propagate itself in the absence of carrier material in a polluted medium.

It is also an object of the invention to provide a composition, for treating a medium contaminated with a chemical pollutant, comprising inoculum of a microorganism having the capacity to degrade a chemical pollutant in combination with a suitable carrier.

It is a further object of the invention to provide a composition, for treating a medium contaminated with a chemical pollutant, comprising inoculum of a microorganism having the capacity to degrade a chemical pollutant in combination with a source of one or more nutrients for the microorganism and a suitable carrier.

It is a further object of the invention to provide a pure culture of M. troyanus strain no. 216–1867, having the capacity to degrade a chemical pollutant.

It is a further object of the invention to provide a pure culture of M. troyanus having the capacity to degrade a polycyclic aromatic hydrocarbon.

It is a further object of the invention to provide a pure culture of M. troyanus having the capacity to degrade benzo[a]pyrene to water soluble metabolites.

It is a further object of the invention to provide a pure culture of M. troyanus having the capacity to degrade and mineralize benzo[a]pyrene.

It is a further object of the invention to provide a composition for treating a medium contaminated with a chemical pollutant, comprising inoculum of M. troyanus having the capacity to degrade a chemical pollutant.

It is a further object of the invention to provide a method of applying a source of one or more nutrients for one or more microorganisms to a contaminated medium, wherein the nutrient(s) are in combination with a carrier material.

It is a further object of the invention to provide a method of applying one or more nutrients to a contaminated medium, wherein the nutrients) are encapsulated within a carrier.

It is a further object of the invention to provide a method of treating a medium contaminated with a chemical pollutant, in which the polluted medium is contacted with inoculum of a microorganism having the capacity to degrade the pollutant.

It is a further object of the invention to provide a method of treating a medium contaminated with a chemical pollutant, in which the polluted medium is contacted with inoculum of a microorganism in combination with a carrier and a source of one or more nutrients for the microorganism.

It is a further object of the invention to provide a method of treating a medium contaminated with a chemical pollutant, in which the polluted medium is contacted with inoculum of a microorganism, and a source of one or more nutrients for the microorganism is added to the medium in combination with a carrier.

It is a further object of the invention to provide a method of treating a medium contaminated with a chemical pollutant, in which the polluted medium is contacted with inoculum of M. troyanus.

It is a further object of the invention to provide a method of treating a medium contaminated with a polycyclic aromatic hydrocarbon, in which the contaminated medium is contacted with inoculum of M. troyanus.

It is a further object of the invention to provide a method of treating a medium contaminated with benzo[a]pyrene, in which the contaminated medium is contacted with a pure culture of M. troyanus strain no. 216-1867 having the capacity to degrade and mineralize benzo[a]pyrene.

It is a further object of the invention to provide a commercially acceptable method of inoculating a medium contaminated with a chemical pollutant with an organism capable of degrading a chemical pollutant.

It is a further object of the invention to provide a convenient, commercially feasible method of establishing a microorganism, capable of degrading a chemical pollutant, in a medium contaminated with the chemical pollutant and having an indigenous microflora.

One feature of the invention is that it provides a composition, comprising viable inoculum of a microorganism having the capacity to degrade a chemical pollutant, for introduction to a medium contaminated with the chemical pollutant.

Another feature of the invention is that it provides a composition, comprising viable inoculum of a microorganism having the capacity to degrade a chemical pollutant in combination with a carrier material, for introduction to a medium contaminated with the chemical pollutant.

Another feature of the invention is that it provides a composition, comprising viable inoculum of a microorganism having the capacity to degrade a chemical pollutant in combination with one or more nutrients for the microorganism and a carrier material, for introduction to a medium contaminated with the chemical pollutant.

Another feature of the invention is that it provides a composition, comprising viable inoculum of a microorganism having the capacity to degrade a chemical pollutant encapsulated within a carrier material, for introduction to a medium contaminated with the chemical pollutant.

Another feature of the invention is that it provides a composition comprising viable inoculum of a microorganism having the capacity to degrade a chemical pollutant in combination with one or more nutrients for the microorganism, in which the microorganism and the one or more of the nutrients are encapsulated within a carrier material.

Another feature of the invention is that it provides a pure culture of M. troyanus strain no. 216-1867 having the capacity to degrade a chemical pollutant.

Another feature of the invention is that it provides a composition comprising viable inoculum of M. troyanus having the capacity to degrade a chemical pollutant.

Another feature of the invention is that it provides a composition comprising viable inoculum of *M. troyanus* having the capacity to degrade a chemical pollutant in combination with a carrier material.

Another feature of the invention is that it provides a method of formulating viable inoculum of a microorganism having the capacity to degrade a chemical pollutant for introduction to a medium contaminated with the chemical pollutant.

Another feature of the invention is that it provides a method of formulating viable inoculum of a microorganism having the capacity to degrade a chemical pollutant in combination with a carrier material.

Another feature of the invention is that it provides a method of formulating viable inoculum of a microorganism having the capacity to degrade a chemical pollutant in combination with one or more nutrients for the microorganism and a carrier material.

Another feature of the invention is that it provides a method of formulating viable inoculum of a microorganism having the capacity to degrade a chemical pollutant encapsulated within a carrier material for introduction to a medium contaminated with the chemical pollutant.

Another feature of the invention is that it provides a method of formulating viable inoculum of a microorganism having the capacity to degrade a chemical pollutant in combination with one or more nutrients for the microorganism, in which the microorganism and one or more of the nutrients are encapsulated within a carrier material.

Another feature of the invention is that it provides a method of delivering a source of one or more nutrients for one or more microorganisms to a contaminated medium, wherein the source of one or more nutrient(s) is in combination with a carrier.

Another feature of the invention is that it provides a method of applying one or more nutrients to a contaminated medium, wherein the nutrient(s) are encapsulated within a carrier.

Another feature of the invention is that it provides a method of treating a medium contaminated with a chemical pollutant, in which the polluted medium is contacted with inoculum of a microorganism having the capacity to degrade the pollutant.

Another feature of the invention is that it provides a method of treating a medium contaminated with a chemical pollutant, in which the polluted medium is contacted with inoculum of a microorganism in combination with a carrier and one or more nutrients for the microorganism.

Another feature of the invention is that it provides a method of treating a medium contaminated with a chemical pollutant, wherein the one or more nutrients are applied to the medium in combination with a carrier.

Another feature of the invention is that it provides a method of treating a medium contaminated with a chemical pollutant, in which the polluted medium is contacted with inoculum of a microorganism and one or more nutrients for the microorganism are added to the medium in combination with a carrier.

Another feature of the invention is that it provides a method of treating a medium contaminated with benzo[a]pyrene in which the contaminated medium is contacted with inoculum of *M. troyanus* having the capacity to degrade benzo[a]pyrene.

Another feature of the invention is that it provides a method of treating a medium contaminated with benzo[a]pyrene in which the contaminated medium is contacted with inoculum of *M. troyanus* having the capacity to degrade benzo[a]pyrene in combination with a carrier.

Another feature of the invention is that it provides a method of treating a medium contaminated with benzo[a]pyrene in which the contaminated medium is contacted with a composition comprising inoculum of *M. troyanus* having the capacity to degrade benzo[a]pyrene in combination with one or more nutrients and a carrier.

One advantage of the invention is that inoculum of a microorganism having the capacity to degrade a chemical pollutant can be preserved for subsequent use in bioremediation.

Another advantage of the invention is that inoculum of a microorganism having the capacity to degrade a chemical pollutant can be protected from predatory organisms following introduction into soil.

Another advantage of the invention is that when encapsulated within a suitable carrier material, a microorganism having the capacity to degrade a chemical pollutant may remain dormant for an extended period of time in the presence of one or more nutrients for the microorganism.

Another advantage of the invention is that when encapsulated within a suitable carrier material, a microorganism having the capacity to degrade a chemical pollutant and which has remained dormant for an extended period of time in the presence of one or more nutrients for the microorganism may become metabolically active by exposing the carrier material to moisture.

Another advantage of the invention is that a microorganism encapsulated within a carrier material, and introduced into a polluted medium, may grow from the carrier material and propagate itself within the polluted medium in the absence of a carrier material.

Another advantage of the invention is that inoculum of a microorganism having the capacity to degrade a chemical pollutant can be encapsulated within a carrier material in combination with one or more nutrients for the microorganism, wherein the one or more nutrients are available to the encapsulated microorganism but are either unavailable or less available to other non-encapsulated microorganisms.

Another advantage of the invention is that a pure culture of *M. troyanus* has the capacity to degrade a chemical pollutant.

Another advantage of the invention is that a pure culture of *M. troyanus* has the capacity to degrade a polycyclic aromatic hydrocarbon to water-soluble metabolites.

Another advantage of the invention is that a pure culture of *M. troyanus* has the capacity to degrade and mineralize benzo[a]pyrene.

Another advantage of the invention is that a pure culture of *M. troyanus* having the capacity to degrade a polycyclic aromatic hydrocarbon can be combined with a carrier material in combination with one or more nutrients for the *M. troyanus*.

Another advantage of the invention is that a pure culture of *M. troyanus* having the capacity to degrade benzo[a]pyrene can be encapsulated within a carrier material for introduction into, and colonization of, a medium contaminated with benzo[a]pyrene.

Another advantage of the invention is that a pure culture of *M. troyanus* having the capacity to degrade benzo[a]pyrene can be encapsulated within a carrier material in combination with one or more nutrients for the *M. troyanus*,.

wherein the one or more nutrients are available to the encapsulated *M. troyanus* but are either unavailable or less available to other non-encapsulated microorganisms.

These and other objects, advantages, and features of the present invention are accomplished by the provision of a pure culture of *M. troyanus* strain no. 216-1867 having the capacity to degrade a polycyclic aromatic hydrocarbon.

These and other objects, advantages, and features of the present invention are accomplished by the provision of a composition comprising a microorganism having the capacity to degrade a chemical pollutant in combination with a source of one or more nutrients for the microorganism.

These and other objects, advantages, and features of the present invention are accomplished by the provision of a composition comprising *M. troyanus* having the capacity to degrade a chemical pollutant.

These and other objects, advantages, and features of the present invention are accomplished by the provision of a method of formulating inoculum of a microorganism having the capacity to degrade a chemical pollutant for introduction of the microorganism into a polluted medium.

These and other objects, advantages, and features of the present invention are accomplished by the provision of a composition comprising a microorganism having the capacity to degrade a chemical pollutant in combination with a source of one or more nutrients for the microorganism, wherein the microorganism and the source of one or more nutrients are encapsulated within a carrier material, and the one or more nutrients are available to the encapsulated microorganism but are either unavailable or less available to other non-encapsulated organisms.

These and other objects, advantages and features of the present invention are accomplished by the provision of a composition comprising a microorganism having the capacity to degrade a chemical pollutant, in which the microorganism is encapsulated within a carrier material when introduced into a polluted medium having an indigenous microflora; and the microorganism further has the capacity to subsequently grow to the perimeter of the encapsulating material, to sporulate thereat, and to release spores which are able to germinate, thereby propagating the microorganism in the medium and external to the encapsulating carrier material.

These and other objects, advantages, and features of the present invention are accomplished by the provision of a method of formulating inoculum of a microorganism having the capacity to degrade a chemical pollutant for introduction of the microorganism into a polluted medium.

These and other objects, advantages, and features of the present invention are accomplished by the provision of a method of remediating a medium contaminated with a chemical pollutant, in which the contaminated medium is contacted with a microorganism having the capacity to degrade the chemical pollutant.

These and other objects, advantages, and features of the present invention will become more apparent from the following description of embodiments thereof.

BRIEF DESCRIPTION OF THE DRAWINGS

FIGS. 1A and 1B show the structures of benzo[a]pyrene and its diol epoxide derivative.

FIG. 2 is a graph comparing the levels of lignin peroxidase in *Phanerochaete chrysosporium* mycelium cultured in vitro and in soil treated with an alginate gel bead formulation of *P. chrysosporium.*

FIG. 3 is a graph showing the time-course of benzo[a]pyrene degradation in liquid cultures of *M. troyanus* strain no. 216-1867, wherein each 50 ml culture contained initially 1 mg of benzo[a]pyrene.

FIG. 4 is a graph showing the time-course of mineralization of $^{14}C$ benzo[a]pyrene in liquid cultures of *M. troyanus* strain no. 216-1867, wherein each 50 ml culture contained initially 1 mg of benzo[a]pyrene.

FIG. 5A is an HPLC elution profile of an ethyl acetate extract of a liquid culture of *M. troyanus* strain no. 216-1867 incubated with $^{14}C$ labelled benzo[a]pyrene for a period of 30 days.

FIG. 5B is an HPLC elution profile of an ethyl acetate extract of an uninoculated control culture containing $^{14}C$ labelled benzo[a]pyrene.

DETAILED DESCRIPTION OF THE PREFERRED EMBODIMENTS

The key role of many species of microorganisms in enacting biogeochemical change has long been recognized. For example, bacteria and fungi are the primary agents in the decomposition of waste materials and the remains of other organisms, and as such are of vital importance in the cycling of matter. Thus in the carbon cycle, organic compounds are subjected to oxidative catabolism by the combined metabolic activity of the microflora in the environment, eventually leading to the conversion of organic carbon to carbon dioxide. Many aerobic bacteria and fungi are capable of utilizing common components of other organisms (such as various lipids, carbohydrates, and proteins) as a source of carbon and energy thereby bringing about the decomposition of these materials. Only certain specialized microorganisms, however, are capable of decomposing more exotic organic compounds, including toxic naturally occurring compounds and chemically complex xenobiotics (see, for example, M. Alexander, "Biodegradation of chemicals of environmental concern," *Science* 211:132–138, 1981; G. Chaudry (Ed.) "*Biological degradation & bioremediation of toxic chemicals," Dioscorides Press, Portland, Oreg.,* 1994).

Bioremediation is a process for environmental cleanup in which microorganisms, which may be either indigenous or introduced, are responsible for the removal or decomposition or degradation of chemical pollutants from contaminated sites. Microorganisms used for bioremediation are often highly specialized metabolically. The decomposition of chemical pollutants by a given microorganism is normally a function of its specific complement of degradative or catabolic enzymes, which in turn is a reflection of the phenotype and genotype of the microorganism.

Microorganisms having the capacity to detoxify, decompose or degrade chemical pollutants and which may be used in bioremediation of a polluted site, may be isolated elsewhere and be subsequently introduced to the polluted site, or they may already be present at the polluted site at relatively low levels and/or be present in a metabolically inactive state. Such microorganisms may be collectively referred to, in general terms, as degradative microorganisms. Degradative microorganisms, which have been isolated from the polluted site or obtained elsewhere, may be used in their native form (i.e. without attempting to change their metabolic characteristics), or they may be changed phenotypically and/or genotypically, in order to increase their effectiveness, prior to their use in bioremediation. Thus, microorganisms deemed potentially useful as agents of bioremediation may undergo enrichment culture in the presence of a chemical pollutant, or in the presence of an analogue of a chemical pollutant, or the microorganisms may undergo mutation, for example by exposure to a known mutagen, or the microorganisms may be genetically manipulated using various recombinant DNA techniques (see, for example, T. Maniatis et al., *Molecular Cloning: A Laboratory Manual*, 1982, Cold Spring Harbor Lab, Cold Spring Harbor, N.Y.)

Once a microorganism with the desired ability to detoxify and/or decompose a toxic chemical pollutant has been obtained using one, or a combination, of the techniques outlined above, in order to remediate contaminated soil in situ, it is necessary to introduce the microorganism to the soil. Further, it is necessary for the introduced microorganisms to survive and remain metabolically active following their introduction into the soil. Still further, once the desired microorganisms have been introduced into the soil, it is necessary for them to grow and proliferate in order to effect an efficient and timely remediation.

The process of bioremediation offers the potential of a cost-effective and environmentally benign method of cleaning up the many sites worldwide which are contaminated by chemical pollutants. In some cases, bioremediation results in mineralization of a chemical pollutant, that is, the complete degradation of a pollutant to yield water and carbon dioxide (see, for example, M. Alexander "Biodegradation of chemicals of environmental concern," *Science* 211:132–138, 1981; J. A. Bumpus (1990) "Microbial degradation of environmentally persistent organopollutants: recent progress and future promise," In: *Biotechnology and Biodegradation*, D. Kamely et al. (eds.) Portfolio Pub. Co., Woodlands, Tex., pp. 59–84; M. A. Providenti et al. "Selected factors limiting the microbial degradation of recalcitrant compounds," *Journal of Industrial Microbiology* 12:379–395, 1993).

Chemical pollutants which have been successfully treated by bioremediation include benzene, toluene, and xylene (BTX aromatics); certain pesticides; and explosives. G. Chaudry (Ed.) "*Biological degradation & bioremediation of toxic chemicals*," Dioscorides Press, Portland, Oreg., 1994). However, a common factor which tends to limit the efficacy of currently used bioremediation processes is the diminution in numbers of the introduced degradative microorganisms over time. Furthermore, in order to accomplish efficient remediation, the degradative organism should preferably propagate itself and effectively colonize the polluted medium. Thus, a major obstacle to effective bioremediation using prior art techniques is the delivery of inoculum of a particular microorganism capable of degrading a pollutant to a contaminated site such that the microorganism not only survives but also propagates itself within the contaminated medium.

The majority of microorganisms used for bioremediation are bacteria (i.e. prokaryotes, mostly unicellular). D. D. Hale, et al., "Biodegradation of chlorinated homocyclic and heterocyclic compounds in anaerobic environments," in *Biological degradation and bioremediation of toxic chemicals*, Ed. G. Chaudry, Dioscorides Press, Portland, Oreg., 1994; R. M. Atlas, et al., "Bioremediation of petroleum pollutants. Diversity & environmental aspects of hydrocarbon degradation," *Bioscience*, 45:332–339, 1995. However, a number of fungi (i.e. eukaryotes, mostly multicellular) are also capable of degrading complex organic compounds, and are potentially valuable as agents for effecting bioremediation. Indeed, fungi which secrete extracellular degradative enzymes have the advantage of having the capacity to degrade a toxic chemical pollutant without being directly exposed to the toxin, exposure to which may adversely affect growth and metabolism. In contrast, bacterial enzymes are predominantly intracellular, and therefore degradation of a toxic chemical pollutant by bacteria ordinarily requires the pollutant to enter the bacterial cell where it has the potential to inhibit growth and metabolism. Moreover, extracellular enzymes of fungi have the potential to degrade compounds with low solubility, and compounds which cannot enter cells. Thus, although some bacteria are efficient degraders of low molecular weight hydrocarbons, higher molecular weight hydrocarbons are generally not degraded efficiently by bacteria, whereas several fungi do show the ability to degrade higher molecular weight hydrocarbons.

Another advantage of fungi as agents for bioremediation is their growth habit as thread-like hyphae and their multicellularity which allows them to penetrate and colonize substrates. Finally, fungi generally exhibit lower substrate specificity, as compared with bacteria, in the degradation of complex organic compounds. This lower substrate specificity of fungi has the potential for the degradation of a plurality of different chemical pollutants, either at the same site or at different sites, with the same fungal species or strain.

Lignin is an important component of the cell walls of vascular plants as a constituent of cell walls of xylem, roots, fruits, buds, bark, and cork. Apart from its role in the formation of supporting and conducting tissues, lignin serves to protect other plant components from chemical, physical, and biological attack. Thus, lignin resists degradation by most microorganisms but is degraded by specialized lignicolous microbes. Lignin represents a class of high molecular weight polymers, comprising monomers of a phenylpropane residue. There are several structural variations of the phenylpropane residue, and numerous ways in which they can be linked together. Further, the polymerization process occurs randomly. Therefore there exists great diversity in the structure of lignin molecules, to the extent that each lignin molecule may in fact be unique. This chemical diversity of lignin explains the non-specific and non-stereo selective nature of lignolytic enzymic activity exhibited by many lignolytic microorganisms. In turn, the capacity of these organisms for non-specific degradation of complex ring compounds signals the potential of lignolytic microorganisms, as a group, for bioremediation of a broad range of pollutants.

One of many fungi having potential as an agent for bioremediation is the white rot fungus *Phanerochaete chrysosporium*. This fungus, a natural inhabitant of forest ecosystems where it occurs on dead or decaying wood, possesses powerful lignolytic enzymic activity. As noted above, *P. chrysosporium* has the ability to degrade a number of toxic chemicals, including several common pollutants of the soil (T. Fernando & S. Aust, "Biodegradation of toxic chemicals by white rot fungi," in *Biological degradation and bioremediation of toxic chemicals*, pp. 386–400, Ed. G. P. Chaudry, Dioscorides Press, Portland, Oreg., 1994; A. Bumpus, et al. "Oxidation of persistent environmental pollutants by a white rot fungus," *Science* 220:1434–1438, 1985. Additionally, *P. chrysosporium* possesses extracellular enzymes which are secreted from the fungal hyphae and are free to diffuse into the medium in advance of the hyphae, thereby allowing for degradation of toxic compounds at sites some distance from the fungal cells, and at the same time the fungus is bestowed with increased tolerance to toxic compounds which are subject to degradation. Furthermore, the ligninase enzymic system of white rot fungi does not require substrate or substrate analogues for induction. Consequently, white rot fungi may not require acclimation to a chemical pollutant, nor a lag period after exposure to a pollutant, in order for degradation of the chemical pollutant to commence.

Despite the potential of *P. chrysosporium* as a bioremediation agent, it has proved difficult using conventional or prior art methods to formulate inoculum of the fungus in such a way that the fungus will establish a population which is sufficiently active and long-lived to be effective in remediating a polluted site. Compositions and methods of the instant invention are disclosed as valuable tools in overcoming this drawback.

Other than *P. chrysosporium*, numerous other microorganisms have the capacity to degrade various chemical pollutants and may be used in conjunction with the instant invention for the purpose of bioremediation. Four organisms which have potential as agents of bioremediation, and their source, are listed in Table 1. A preferred organism for bioremediation, under the invention is *M. troyanus* strain no. 216-1867. However, recitation of the above organisms or those listed in Table 1 should not be construed as limiting the invention in any way; rather attention is drawn to the claims appended hereto which serve to define the scope of the invention.

The instant invention is concerned with compositions comprising inoculum of microorganisms useful as agents for bioremediation and methods for formulating such compositions. The instant invention is also concerned with compositions comprising a source of one or more nutrients in combination with one or more carrier materials for facilitating bioremediation and methods for formulating such compositions. The instant invention is also concerned with methods of performing or facilitating bioremediation using the compositions and methods of the instant invention.

A degradative microorganism may be combined with various carriers by mixing a preparation of the microorganism with the carrier material in various ratios to form a more or less homogeneous amorphous mixture. Such a mixture may take the form of a suspension, a paste or the like, depending on the particular carrier and microorganism and the ratios used. Alternatively, the combination of a degradative microorganism with a carrier material may be such that the microorganism is encapsulated by, or enclosed within, the carrier material. In the latter case, encapsulating material may be in a variety of shapes, including more or less flat layers or sheets and spheroidal pellets or beads. In addition, encapsulating materials in combination with a microorganism may be formed in specific ranges of size. The particular shape and size of the encapsulating material will depend on factors such as the nature of the microorganism, the composition of the carrier material, and the intended applications. A broad range of materials may be used as carriers, e.g. silica, peat, certain cereal grains or grain products, water-insoluble gels, and various clays or clay-like materials. Carrier materials may comprise mixtures of two or more of these or other materials. Furthermore, a given carrier material may be used to encapsulate two or more different species or strains of microorganisms in various combinations.

Compositions comprising formulations of microbial inoculum under the invention comprise a microorganism capable of degrading a chemical pollutant in combination with a suitable carrier material. Under the invention, compositions for bioremediation may comprise two or more different species or strains of microorganisms which are able to coexist or are compatible. The two or more different microorganisms may act more or less independently during bioremediation: each organism may itself independently degrade or decompose the same chemical pollutant, or each organism may itself independently degrade or decompose one or more different chemical pollutants present in the same contaminated medium. For example, organisms A and B may both independently degrade compound Y, or organism A may independently degrade compound Y, while organism B may independently degrade compounds W and Z. When each of two or more different compatible organisms degrade or decompose the same chemical pollutant, the biochemical mechanism of degradation or decomposition of the chemical pollutant by the different organisms may be the same or different. Alternatively, two or more different compatible microorganisms comprising a single bioremediation composition may act in concert to degrade a particular chemical pollutant, that is, the two or more different organisms may complement each other metabolically with respect to degradation of the pollutant. For example, a first microorganism of the bioremediation composition may metabolize a toxic chemical pollutant to one or more products, at least one of which may also be toxic. A second microorganism may then metabolize one or more of the metabolic products of the first microorganism.

In one embodiment of the invention, compositions further comprise one or more nutrients. Such nutrients may constitute the sole source of nutrients for the microorganism during a particular period prior to, or during, the bioremediation process, or they may represent nutrients which are supplementary to another source of nutrients. Nutrients to be supplied to a microorganism under the invention may be organic or inorganic, and may represent, for example: a source of energy, a source of carbon, a source of nitrogen, a source of phosphorus, a source of sulfur, a source of growth factors, a source of vitamins, a source of amino acids, a source of purine, a source of pyrimidine, a source of minerals, and a source of micronutrients.

Compositions under the invention may also comprise a wide variety of carrier materials, including either organic or inorganic powdered material, such as peat, clay or silica. Carrier materials under the invention may also be constituted as a gel. Such gel materials comprising a carrier under the invention may be polymeric or copolymeric, and may be derived from either natural sources or from synthetic chemicals. Examples of gel materials which may be used as carrier materials include various salts of alginic acid and polyacrylamide. Two or more materials, including powdered materials and gel materials, may be combined in various proportions to provide a suitable carrier for a microorganism. Compositions under the invention comprising two or more different carrier materials may be homogeneous or heterogeneous with respect to the carrier component. In the latter case compositions may comprise carriers comprising two or more different layers. Compositions comprising one or more carrier materials may be constituted with a suitable liquid, in various ratios, as a pellet, paste, or suspension, and the like. Liquids comprising compositions under the invention may be essentially pure compounds, used either for dissolving or for suspending one or more other components of the composition, for example deionized water. Alternatively, a liquid comprising a composition under the invention may itself comprise one or more compounds dissolved or suspended in the liquid. Thus a liquid comprising a composition under the invention may comprise one or more nutrients for a microorganism suspended or dissolved in a solvent. A preferred solvent under the invention is water.

Microorganisms and/or nutrient(s) comprising compositions under the invention may be admixed with a carrier material to form initially an amorphous, more or less homogeneous mixture, which subsequently may be cut, rolled, extruded, etc. to produce various forms of the composition. Or, the microorganisms and/or nutrient(s) may be encapsulated within the carrier material to form a capsule. It will be clear to the skilled artisan that the specific shape and size of such capsules can be varied, depending on factors such as the nature of the encapsulated microorganism, the intended application of the encapsulated composition, ease of storage and handling, and the like. A preferred carrier material under the invention is a water-insoluble polymeric gel. A particularly preferred carrier is an alginate salt, and more preferably, calcium alginate.

Microorganisms that may be used in the context of the instant invention include various fungi, bacteria, and other organisms that have the capacity to degrade one or more chemical pollutants to less toxic or non-toxic products. Preferably, such organisms are capable of retaining viability for extended periods of time following the formulation of the organism in combination with one or more carrier materials. Preferably, compositions of the instant invention comprising the combination of a degradative microorganism with one or more carrier materials will enable the microorganism to retain viability over an extended period of time during storage either at ambient or reduced temperatures. Furthermore, preferably compositions of the instant invention comprising the combination of a degradative microorganism with one or more carrier materials will enable the microorganism to retain viability over an extended period of time following introduction of the compositions into a medium contaminated with a toxic chemical pollutant and having an indigenous microflora. More preferably, compositions of the instant invention comprising the combination of a degradative microorganism with one or more carrier materials will enable the microorganism to retain viability over an extended period of time, and further, will allow the microorganism to grow away from the one or more carrier materials, to propagate itself, and to produce one or more degradative enzymes, following introduction of the microorganism-containing composition into a medium contaminated with a toxic chemical pollutant and having an indigenous microflora.

A method of formulating a composition comprising a microorganism in combination with a carrier material will now be described in the context of fungal inoculum in combination with an alginate gel carrier. It will be apparent to the skilled artisan that other methods may be used within the scope of the invention for preparing compositions comprising other types of organisms and other carrier materials. It is to be understood that other such methods are within the scope of the instant invention as defined by the claims.

Inoculum of a fungus comprising a composition for bioremediation may be prepared by growing the fungus on any liquid or solid culture medium which will support its growth. However, preferably the culture medium will be one which supports vigorous growth and, optionally, sporulation of the fungus. The composition of the culture medium, aeration rate, incubation temperature, etc. will depend on the particular fungus to be grown for production of inoculum. Those skilled in the art will readily appreciate how these parameters may be successfully manipulated to obtain a suitable source of fungal inoculum. After a suitable period of incubation, the fungus may be harvested by suspending it in either spent liquid medium in which the fungus has been grown or in a sterile liquid, to provide a suspension of fungal inoculum. The fungal inoculum may be in the form of a suspension of mycelial hyphae, spores, or other propagules; or in the form of a suspension comprising a combination of mycelium, spores, and other propagules. In the latter case, the mycelium, spores, and other propagules of the suspension may be separated from each other to provide different types of inoculum suspension prior to adjustment of the concentration of the inoculum. If mycelium is used for preparing the inoculum it may be blended or comminuted to provide a suspension of hyphal fragments. The concentration of the hyphal fragments, spores or other propagules in the suspension may be adjusted to the desired concentration range, normally expressed as colony forming units/ml (cfu/ml). The concentration of inoculum is preferably in the range of $10^3$–$10^9$ cfu/ml, more preferably in the range of $10^5$–$10^8$ cfu/ml.

A sterile liquid used to harvest a fungal culture for preparation of fungal inoculum may be water (tap, deionized, or distilled water) or fresh culture medium. When the sterile liquid used to prepare fungal inoculum is water, it subsequently may be supplemented with any number of organic or inorganic compounds which may serve as a source of at least one nutrient for the fungus. Such compounds which may be added to the preparation of fungal inoculum may serve as a source of at least one nutrient for the fungus in one or more of the following capacities: a source of energy, a source of carbon, a source of nitrogen, a source of phosphorus, a source of sulfur, a source of growth factors, a source of vitamins, a source of amino acids, a source of purine, a source of pyrimidine, a source of minerals, and a source of micronutrients. When fresh culture medium is used to resuspend a fungal culture for preparation of a suspension of fungal inoculum, it may have the same composition, qualitatively and quantitatively, as the culture medium on which the fungus has been grown, that is to say the two culture media are precisely the same with respect to the nutrient components. Alternatively, a second, different medium may be used to resuspend the fungal growth. The composition of the second medium will depend on a number of factors which may include, for example, the microorganism, the pollutant, and the intended site of application. In general, a second, different medium used to prepare fungal inoculum will comprise at least one of the following types of components: a source of energy, a source of carbon, a source of nitrogen, a source of phosphorus, a source of sulfur, a source of growth factors, a source of vitamins, a source of amino acids, a source of purine, a source of pyrimidine, a source of minerals, and a source of micronutrients.

A suspension of fungal inoculum prepared as described above is diluted with a slurry of a water soluble salt of alginic acid in water. A preferred salt of alginic acid under the invention is sodium alginate. The preferred water is distilled water or deionized water. Preferably, the suspension of fungal inoculum is diluted 1:3 (v/v) with a slurry of 0.7–2.5% sodium alginate (by weight) in deionized water to give a final sodium alginate concentration of 0.525–1.875% (by weight). More preferably, the final sodium alginate concentration is in the range of 0.75–1.5% (by weight). Most preferably the final sodium alginate concentration is in the range of 0.9–1.1% (by weight). The mixture may be amended by the addition of various inorganic or organic materials, including, for example, a source of at least one nutrient for the microorganism, and/or supplementary water absorbent materials or fillers such as clay, ground silica, sawdust, corncob grits, and the like. It is to be understood that certain carrier materials, as well as certain water absorbent materials or fillers can also serve as a direct source of at least one nutrient for the microorganism. That is to say, certain components of an inoculum composition under the invention may play a dual role as a source of at least one nutrient for the microorganism and as a supplementary water absorbent filler or carrier material. For example, a carrier material such as alginate gel may play a dual role as a vehicle or encapsulating agent for a microorganism and as a reservoir for the slow release of micronutrients required for the growth of microorganisms. In particular, the addition of suitable proportions of certain supplementary water absorbent materials to the fungal inoculum/sodium alginate mixture may serve to enhance survival of the microorganism within the carrier material, and may also promote establishment of the microorganism in the environment into which it has been introduced.

The advantages associated with the addition of supplementary water absorbent materials to the composition must, however, be tempered by the fact that increases in their concentration beyond a certain critical level tends to seriously compromise the integrity of the resultant alginate gel capsule or bead, and furthermore, tends to prevent passage of the inoculum/alginate mixture through a relatively small orifice (according to the technique of forming the gel beads, as described below). The concentration of supplementary water absorbing materials that may compromise capsular integrity depends on a number of factors, including the nature of the supplementary material and the concentration of the sodium alginate. As a general rule, however, the concentration of supplementary water absorbent materials in the composition will preferably not exceed 20% (w/v), more preferably the concentration will not exceed 12% (w/v), and most preferably the concentration will not exceed 8% w/v.

The inoculum mixture comprising sodium alginate, and optionally further comprising a source of one or more nutrients and further optionally comprising one or more supplementary water-absorbent materials or fillers, is added dropwise to a bath containing a metal cation solution. Contact of each drop of the inoculum/alginate mixture with the metal cation solution causes gelation of the mixture and entrapment of components of the composition within the resulting gel matrix. The size of the orifice from which drops of the inoculum/alginate mixture are formed may be varied over a fairly broad range of 0.1–4.0 mm, preferably 0.5–2.0 mm, and will influence the size of the resultant gel beads formed upon contact of the drops with the metal cation solution. Metal cations comprising the metal cation solution include $Al^{2+}$, $Ba^{2+}$, $Ca^{2+}$, $Cu^{2+}$, and $Zn^{2+}$, or possibly mixtures of these cations. A preferred metal cation solution comprises a $Ca^{2+}$ salt. A preferred method is to keep all components sterile prior to addition of the microorganisms. As will be apparent to the skilled artisan, parameters such as the volume of the sodium alginate containing drops, and the nature and ionic strength of the metal cation solution, may be varied within certain ranges which may be determined empirically. It should be understood, however, that the net effect of such parameters should ordinarily result in gelation of a substantial part of the entire bead, proceeding from the bead surface toward the center. When $Ca^{2+}$ is the cation comprising the metal cation solution, the preferred cation concentration of the solution is 0.1–1.0M, and more preferably 0.2–0.3M. Adequate gelation of the bead preferably occurs within 0.1–15 minutes of contacting the metal cation solution, more preferably within 2–5 minutes. The beads are dried and become granules. Either hydrated, undried alginate beads or dried beads (=granules, pellets, or prills) can be used in practice.

The encapsulation technique described above provides inoculum of a degradative microorganism, which inoculum typically is evenly distributed throughout the gel bead or granule; is capable of retaining viability for an extended period of time; may be conveniently stored for subsequent use; may provide a source of nutrients to the entrapped microorganisms; buffers the microorganism against extremes of pH, water activity levels, and the like; and also provides protection against predatory organisms. Moreover, the granule formulation as disclosed herein permits an entrapped microorganism to propagate itself outside the granule.

Propagation of an alginate encapsulated fungus outside the granule may take place to various extents. For example, at a basic level of colonization of the soil or other medium, or during an early stage of colonization, fungal mycelium may simply be present, in greater or lesser profusion, on the surface of the granule. An intermediate degree of fungal colonization is represented by a situation where mycelial growth of the fungus from a plurality of granules results in hyphal connections being formed from one bead to the next, and so on, thereby resulting in a form of reticulate fungal-metabolic framework within the soil. This intermediate level of colonization is seen, for example, in the case of *M. troyanus* ten days after introduction of the fungal formulation into soil, according to Example 6. At a more advanced level or stage of fungal colonization, secondary and tertiary propagation events may occur, leading to extensive colonization of the soil by the introduced fungus. Such advanced colonization may occur according to the following series of events:

i) a first phase of vegetative growth of the microorganism through the hydrated granule or gel bead to the perimeter of the bead and thence into the polluted medium, ii) after item i), production of a first plurality of propagules, and iii) after item ii), release of said first plurality of propagules at a primary location within the polluted medium, and said first plurality of propagules are capable of:

iv) dissemination within the polluted medium to a secondary location more or less distant from the primary location whence said first plurality of propagules originated, and V) germination to initiate a second phase of vegetative growth, said second phase of vegetative growth capable of spreading the microorganism within the polluted medium, and said second phase of vegetative growth capable of production of a second plurality of propagules. Said second plurality of propagules are capable of being disseminated within the polluted medium as recited in item iv), and are further capable of germination to reinitiate vegetative growth, thereby completing a cycle of events which may be repeated a plurality of times resulting in colonization.

At each stage, phase, or level of colonization of a polluted medium by an introduced microorganism as referred to above, vegetative growth and/or propagules may produce one or more intracellular or extracellular degradative enzymes. The ability of an introduced fungus to propagate itself and colonize a polluted medium is necessary for an efficacious in situ bioremediation process, since contact of the mycelium, or extracellular enzymes emanating therefrom, with the pollutant is required for degradation of the pollutant; and, colonization of the polluted medium provides a larger area of mycelium and allows extracellular enzymes to contact a larger volume of pollutant.

Inoculum of *P. chrysosporium* hyphal fragments formulated with corncob grits and encapsulated within alginate granules was capable of retaining viability for a period of at least 50 weeks at 5° C., and was able to colonize non-sterile soil. Inoculum of *P. chrysosporium* spores formulated in the same manner was capable of retaining viability for a period of at least 25 weeks at ambient temperature, and was also able to colonize non-sterile soil. Mycelial growth of *P. chrysosporium* in non-sterile soil following introduction of inoculum compositions was positive for ligninase production, as determined by an ELISA assay.

Formulation of inoculum of *P. chrysosporium* and *M. troyanus* with alginate gel, and retention of viability and ability to propagate within soil exhibited by inocula, is illustrated in Examples 1–4.

Determination of the kinetics of induction/release and longevity of lignolytic enzymes upon introduction of fungal/alginate formulations into soil can be achieved through the use of the enzyme-linked immunosorbent assay (ELISA) technique. Studies were conducted to determine the presence of these enzymes in a soil environment and to develop a method to monitor the degradative process over time, as described in Example 6.

According to one embodiment of the invention, compositions may comprise a source of one or more nutrients for a microorganism capable of degrading a chemical pollutant, and a carrier for the source of one or more nutrients. Such a composition may be added to a polluted medium which is subject to in situ bioremediation by one or more degradative microorganisms, where the composition may provide for the controlled release of one or more nutrients for use by one or more microorganisms over an extended period of time.

Apart from the introduction of microbial inoculum into a polluted medium, such as soil, other bioremediation technologies include bioreactors, land farming, and composting (see, for example, P. Morgan & R. J. Watkinson, "Hydrocarbon degradation in Soils and Methods for Soil Biotreatment," *CRC Critical Reviews in Biotechnology* 8:305–333, 1989). For example, bioreactors containing one or more different microorganisms having the capacity to degrade one or more pollutants may be used for the ex situ bioremediation of polluted groundwater, such as groundwater contaminated with hydrocarbons or other petroleum derived products. organic pollutants tend to accumulate in the upper layers of groundwater. Water from different layers of groundwater may be selectively pumped or otherwise removed from the ground, depending on the circumstances including the degree and nature of the contaminants, the capability of the degradative microorganism(s), the nature and capacity of the bioreactor, and the projected end-use of the remediated water. Contaminated water may be circulated through a bioreactor, at an appropriate rate, where removal or degradation of one or more pollutants is enacted by the resident microflora. Effluent from the bioreactor may be used directly, stored separately from the groundwater reservoir, or returned to deeper, less contaminated layers of groundwater.

Degradative microorganisms for use in bioreactors may be formulated in various ways in order to maintain their viability and metabolic activity. Compositions comprising degradative microorganisms and methods of making such compositions, under the invention, for use in bioreactors or other ex situ bioremediation processes may be performed essentially as described above in the context of in situ bioremediation of soil. A preferred formulation of degradative microorganisms for use in bioreactors under the invention is encapsulating alginate gel beads. A preferred microorganism for use in bioreactors under the invention is *M. troyanus*. A more preferred microorganism for use in bioreactors under the invention is *M. troyanus* strain no. 216-1867.

Because of the widespread occurrence and carcinogenicity of benzo[a]pyrene, various fungal species representing diverse taxa have been screened for their ability to degrade this compound, to reveal several species which are capable of degrading this compound. D. Datta & T. A. Samanta "Effect of inducers on metabolism of benzo[a]pyrene in vivo and in vitro: analysis by high pressure liquid chromatography," *Biochem. Biophys. Res. Comm.* 155:493–502, 1988; C. E. Cerniglia & D. T. Gibson "Fungal oxidation of (+) 9,10-dihydroxy-9,10-dihydrobenzo[a]pyrene. Formation of diastereomeric benzo[a]pyrene 9,10 diol 7,8-epoxides," *Proc. Natl. Acad. Sci.* 77:4554–4558, 1980; P. Morgan, et al. "Comparison of abilities of white rot fungi to mineralize selected xenobiotic compounds," *Appl. Microbiol. Biotechnol.* 34:693–696, 1991; J. A. Field, et al., "Biodegradation of polycyclic aromatic hydrocarbons by new isolates of white rot fungi." *Appl. Environ. Microbiol.* 58: 2219–2226, 1992. Several of the fungal species having the capacity to degrade benzo[a]pyrene are white rot fungi, including *P. chrysosporium* (J. A. Bumpus, et al., "Oxidation of persistent environmental pollutants by a white rot fungus," *Science*, 28:1434–1436, 1985); *Trametes versicolor* (P. Morgan, et al., "Comparison of abilities of white rot fungi to mineralize selected xenobiotic compounds," *Appl. Microbiol Biotechnol.*, 34: 693–696, 1991); and Ramaria sp. (J. A. Field, et al., "Biodegradation of polycyclic aromatic hydrocarbons by new isolates of white rot fungi," *Appl. Environ. Microbiol.*, 58:2219–2226, 1992).

Prior to the instant invention, most studies on the degradation of polycyclic aromatic pollutants focused on *P. chrysosporium* (see, for example, J. A. Bumpus, et al., "Oxidation of persistent environmental pollutants by white rot fungus," *Science* 220:1434–1438, 1985; Haemmerli, S.D., et al., "Oxidation of benzo[a]pyrene by extracellular ligninase of *Phanerochaete chrysosporium*," *J. Biol. Chem.*, 261:6900–6903, 1986; J. B. Sutherland, et al., "Metabolism of phenanthrene by *Phanerochaete chrysosporium*," *Appl. Environ. Microbiol.*, 57:3310–3316, 1991; Barr, D. P. & Aust, S. D., "Mechanisms white rot fungi use to degrade pollutants," *Environ. Sci. Technol.*, 28:78–87, 1994).

To the best of our knowledge, members of the genus Marasmiellus have not previously been used in studies on degradation of toxic chemical pollutants. We have now discovered that *Marasmiellus troyanus* has the ability to degrade and mineralize the mutagenic polycyclic hydrocarbon benzo[a]pyrene.

A fruiting body of Marasmiellus sp. was collected from partially decomposed leaf litter from the site of the abandoned Inger oil refinery in Darrow, La. This refinery experienced a major spill of used oil in 1978 and was declared a Superfund site in 1982. The Inger site is known to be contaminated with benzo[a]pyrene. Spores of the Marasmiellus sp. were germinated on malt extract agar, and stock cultures were maintained on potato dextrose agar. This isolate was identified as *M. troyanus* and designated strain no. 216-1867. A deposit of this culture was made with the Northern Regional Research Center of the USDA, Peoria, Ill., under the Budapest Treaty. The NRRL accession number is 21547. It was deposited on Mar. 25, 1996.

Figure 3:
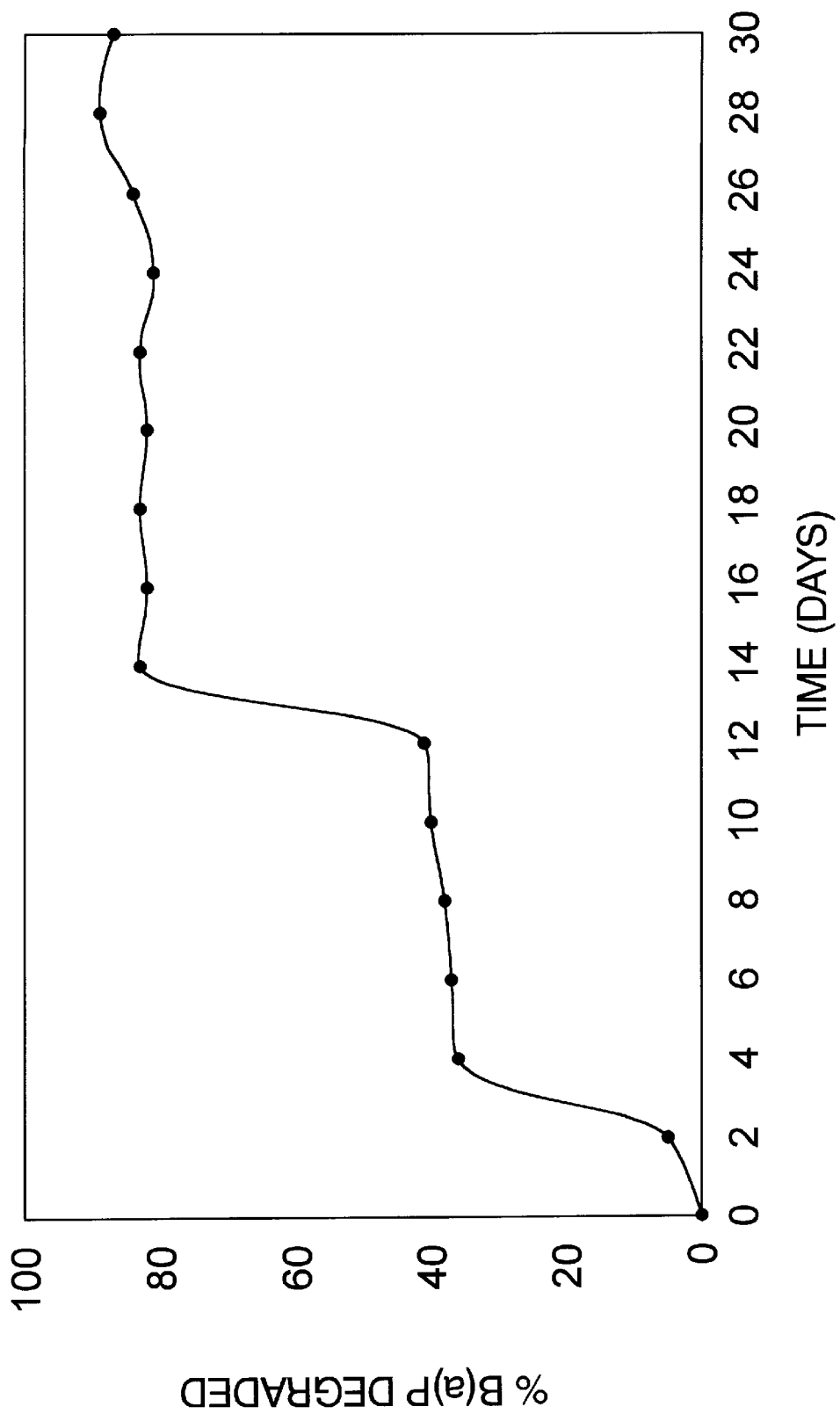

Mycelium of *M. troyanus* strain no. 216-1867 harvested from broth cultures was added to distilled water and incubated with an authentic standard of benzo[a]pyrene. Degradation of benzo[a]pyrene was determined periodically by HPLC analysis of organic extracts of the distilled water cultures, clearly demonstrating the degradation of benzo[a]pyrene by *M. troyanus* The vast majority of the total benzo[a]pyrene was degraded within a period of two weeks (FIG. 3). The experimental details of the determination of benzo[a]pyrene degradation by *M. troyanus* are presented in Example 8.

It can be seen from the graph in FIG. 3 that degradation of benzo[a]pyrene by *M. troyanus* strain no. 216-1867 under the experimental conditions presented in Example 8, is biphasic. In particular, there is an initial lag period of approximately 2 days following exposure of mycelium of *M. troyanus* to benzo[a]pyrene, followed by a period of rapid biodegradation of benzo[a]pyrene until about day 4. There then ensues a second lag period until about day 12, followed by a second phase of rapid biodegradation of benzo[a]pyrene. The kinetics of benzo[a]pyrene degradation shown here indicate the involvement of two separate inducible enzymic systems. Those skilled in the art will appreciate that the particular length of the lag periods described above may be changed by changing cultural parameters, such as the volume of the inoculum, substrate (i.e. benzo[a]pyrene) concentration, temperature, degree of aeration, pH, etc.

In a separate experiment, mycelium of *M. troyanus* strain no. 216-1867 harvested from broth cultures was added to distilled water and incubated with an authentic standard of benzo[a]pyrene spiked with radiolabeled benzo[a]pyrene. Mineralization of benzo[a]pyrene was determined periodically by liquid scintillation counting of radiolabeled $^{14}CO_2$ released from radiolabeled $^{14}C$ benzo[a]pyrene substrate. The results clearly demonstrate the mineralization of benzo[a]pyrene to $CO_2$ by *M. troyanus* The experimental details of experiments demonstrating mineralization of benzo[a]pyrene by *M. troyanus* are presented in Example 9, and the results are presented in FIG. 4.

Figure 4:
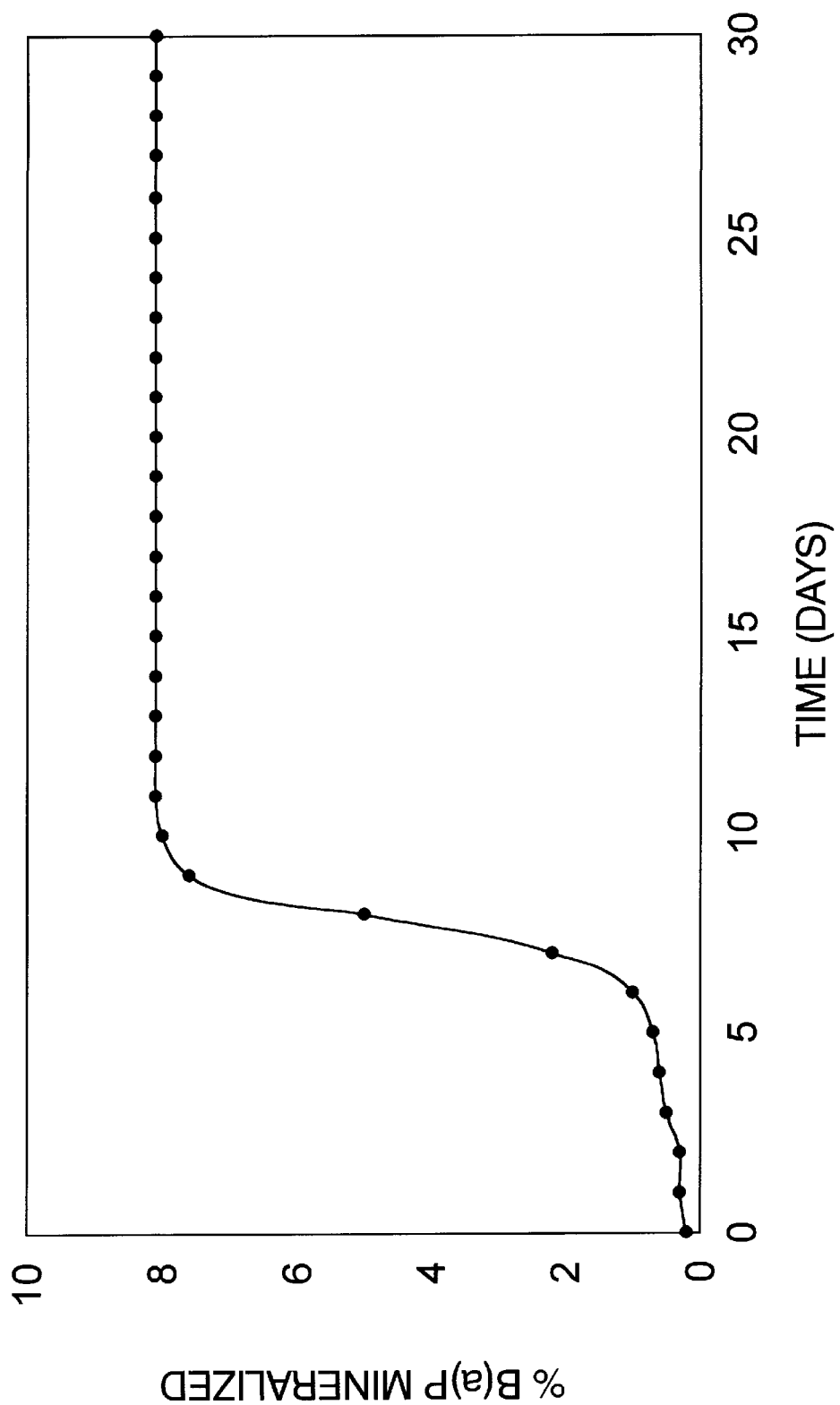

It can be seen from the graph in FIG. 4 that mineralization of benzo[a]pyrene by *M. troyanus* strain no. 216-1867 under the experimental conditions presented in Example 9 occurs after an initial lag period of approximately 5 days following exposure of mycelium of the *M. troyanus* to benzo[a]pyrene. This is followed by a period of rapid mineralization of benzo[a]pyrene until about day 9, after which relatively little further release of radiolabeled $CO_2$ occurs. From a comparison of the time course of events in FIG. 3 and FIG. 4, it can be seen that the end of the first phase of benzo[a]pyrene degradation (FIG. 3) approximately coincides with the mineralization of benzo[a]pyrene (FIG. 4). These results suggest the association of the enzymic system of the first phase of degradation with the mineralization process. In any event, the skilled artisan will appreciate that the length of the lag period prior to mineralization of benzo[a]pyrene by *M. troyanus*, and the total extent of such mineralization, may be changed by manipulation of cultural or environmental parameters, such as the volume of the inoculum, substrate (i.e. benzo[a]pyrene) concentration, temperature, degree of aeration, pH, etc.

In a further separate experiment, the mass balance of radiolabeled materials following incubation of radiolabeled benzo[a]pyrene with mycelium of *M. troyanus* strain no. 216-1867 was studied. After incubation for 30 days, the head space gas was flushed through a $CO_2$ trap for determination of the amount of radioactivity present as $^{14}CO_2$, indicative of the extent of benzo[a]pyrene mineralization. The culture was partitioned between organic and aqueous phases, and the amount of radioactivity present in each phase was also determined. The experimental details of the experiment are presented in Example 10. The results clearly confirm the findings of the experiments described above, that *M. troyanus* strain no. 216-1867 has the ability to both degrade benzo[a]pyrene and to mineralize it to $CO_2$. The results also show that degradation of benzo[a]pyrene by *M. troyanus* results in the formation of at least one, and most probably a number of, water soluble metabolites. In general terms, compounds with increased water solubility are more readily excreted from the body, and consequently are usually less toxic.

The invention is further illustrated by way of the following Examples.

EXAMPLE 1

Part A: Formulation of *P. chrysosporium* mycelium.

*P. chrysosporium* was cultured in 80 ml of malt extract liquid medium (Difco Laboratories, Detroit, Mich.) in a 250 ml Erlenmeyer flask for 7 days at 25° C., and the culture was homogenized for 30 seconds in a sterile blender. Eighty ml of fungal homogenate was combined with 112 g of sodium alginate solution (2 g sodium alginate (Kelgin, Kelco Co., Clark, N.J.) in 110 ml of deionized water). The fungal homogenate/sodium alginate solution was then combined with 8 g of either corncob grits (Anderson Cob, Maumee, Ohio) sawdust, mixed hardwoods (Ipek Door Co., Kenner, La.), or Pyrax clay (Pyrax ABB, R. T. Vanderbilt Co., Inc., Norwalk, Conn.). The mixture was stirred for about 30 min at a pH of 4.5. The mixture was then added dropwise from a Pasteur pipette to a 0.25M solution of $CaCl_2$ to form individual gel beads. After 5 min the gel beads were washed in sterile water and air-dried at ambient temperature overnight. The diameter of the dried beads or granules ranged from 2–4 mm (mean 2.7 mm), and the dry weight of the beads ranged from 5–7 mg (mean 6 mg).

Each of the three different formulations of granules (i.e. containing clay, sawdust or corncob grits) was stored at 5, 25 and 28° C. To assess fungal viability over time, after storage for various periods the granules were plated on malt extract agar, and after incubation the granules were observed for the presence or absence of growth. The viability of alginate-encapsulated *P. chrysosporium* formulated in combination with three different filler materials and stored at either 5, 25 or 28° C. are recorded in Table 2.

Survival of the encapsulated inoculum following introduction into non-sterile soil and capacity to colonize non-sterile soil was assessed by placing each of the three types of granules into two different soil samples, either sandy loam, pH 5.3 (Evesboro AP) or sandy loam, pH 6.6 (Conover AP). Both soil samples are standard samples obtained from the USDA. Both soil samples were supplemented with corncob grits (5 g per 70 g of soil) prior to the introduction of inoculum. For introduction into soil, the granules were placed inside wire mesh packets (25 granules per packet) to facilitate subsequent recovery and observation of the granules. The wire mesh packets containing the granules were at a depth of 2 cm below the soil surface, and the soil was maintained at a moisture content of 80% of maximum water holding capacity and a temperature of 32° C. for two months. The results of the soil viability study were expressed semi-quantitatively on an arbitrary scale, and are presented in Table 2.

It can be seen that all three formulations of *P. chrysosporium* hyphal fragments retained viability after storage at 5° C. for a period of 50 weeks. Inoculum of *P. chrysosporium* hyphal fragments supplemented with either sawdust or corncob grits was able to colonize non-sterile soil samples.

Part B: Formulation of *P. chrysosporium* spores

A spore suspension of *P. chrysosporium* containing about $2.5 \times 10^6$ spores/ml was prepared by flooding a 7–10 day malt extract agar plate with 10 ml of distilled water. The spore suspension was combined with either corncob grits, sawdust or Pyrax clay (Pyrax is pyrophyllite, a hydrous aluminum silicate), and an alginate gel bead formulation of the inoculum was prepared essentially according to Example 1, Part A. The retention of viability during storage at three different temperatures, and survival in non-sterile soil, were assessed essentially as described in Part A. The results are recorded in Table 2, where it can be seen that *P. chrysosporium* was recoverable from samples of all three different formulations of inoculum after storage at 28° C. for 25 weeks. Inoculum of *P. chrysosporium* spores formulated with corncob grits retained viability in non-sterile soil for a period of at least two months (Table 2).

EXAMPLE 2

Inoculum comprising hyphal fragments of *M. troyanus* strain no. 216-1867 was formulated in alginate with either corncob grits, sawdust, or Pyrax clay, essentially according to the methods of Example 1. Retention of viability and survival-in non-sterile soil was assessed as described in Example 1. The results are recorded in Table 2. *M. troyanus* strain no. 216-1867 is a basidiomycete isolated from the site of the abandoned Inger oil refinery, DARROW, La. Inoculum of *M. troyanus* formulated with corncob grits retained viability for 25 weeks during storage at 5° C. The same formulation retained viability in non-sterile soil over a period of two months, and colonized the soil to a distance of at least 1.5 cm from the perimeter of the alginate beads.

EXAMPLE 3

Inocula of *Aspergillus parasiticus, Cunninghamella echinulata* var. elegans, and *Serratia marcesens*, were formulated in alginate with either corncob grits, sawdust, or Pyrax clay, essentially according to the methods of Example 1. Retention of viability and survival in non-sterile soil was assessed as described in Example 1. The results are recorded in Table 2.

*Aspergillus parasiticus*, a member of the Fungi Imperfecti, is commonly found on cereal grains and other food/feed products. *A. parasiticus* retained viability when stored at 5° C. for a period of 25 weeks, but was not recoverable from non-sterile soil.

*Cunninghamella echinulata* var. elegans is a fungus which has been shown to resist chemically hostile environments. Inoculum of *C. echinulata* var. elegans formulated in alginate with sawdust retained viability for at least 25 weeks at 5° C.

Serratia marcesens (KGW-1) is a Gram negative diplococcus bacterium isolated from the Superfund site at the Old Inger Refinery, Darrow, La. *S. marcesens* formulated in alginate with corncob grits retained viability for at least 25 weeks at 5° C. Inocula of *C. echinulata* and *S. marcesens* were not tested for their ability to survive within, or colonize, soil.

EXAMPLE 4

Growth of Fungi from Alginate Beads in Soil Amended with a Carbon Nutrient Source Studies were conducted to enhance fungal colonization of the soil environment from fungal/alginate formulations, according to the following Example.

Growth of fungi encapsulated within gel beads was compared with growth from mycelial agar plugs. Inoculum (gel beads or agar plugs) was placed at a depth of 2 cm. in non-sterilized Conover AP soil in a wide-mouth specimen jar. Each jar contained 70 g of soil amended with 5 g of either corncob grits, sawdust, or bagasse (sugar cane waste) as a carbon source. Fungal/alginate formulations of *P. chrysosporium* mycelium, *P. chrysosporium* spores, or *M. troyanus* mycelium were prepared as described above. Each specimen jar received as inoculum either one packet of 25 gel beads, or of mycelial agar plugs.

Soil moisture was maintained at 80% field capacity, measured by weight. The experiment was conducted at 32° C. for two months, and fungal growth in soil was scored semi-quantitatively using an arbitrary scale (Table 3).

All three formulations, *P. chrysosporium* mycelium, *P. chrysosporium* spores, and *M. troyanus*, grew in soil amended with corncob grits or bagasse. Alginate bead formulations of *P. chrysosporium* mycelium and *M. troyanus* did not grow on sawdust amended soil, while the alginate bead formulation of *P. chrysosporium* spores grew slowly. Mycelial growth in soil was observed after 5–10 days for the beads containing *P. chrysosporium* mycelium. Fungal growth from beads formulated with *P. chrysosporium* spores was first observed at 30 to 40 days. Fungal growth from beads formulated with *P. chrysosporium* spores and with *M. troyanus* was faster in soil amended with corncob grits than in soil amended with sawdust or bagasse. However, the alginate bead formulation of *P. chrysosporium* mycelium grew slightly better in bagasse amended soil, as compared with soil amended with either sawdust or corncob grits, with fungal growth observed on soil after 3 days.

Inoculum comprising mycelial agar plugs of *P. chrysosporium* or *M. troyanus* did not grow in any of the soils tested (Table 3).

EXAMPLE 5

Viability of fungal/alginate Formulations in Polluted Soil

Soil was collected from two locations: Old Inger, Gonzales, La. and Devil's Swamp Bayou, East Baton Rouge, La. Chemical contaminants in the soil at these sites include: polyaromatic hydrocarbons, such as benzo[a] pyrene, and heavy metals. Soil samples were collected from two sites at each location. The soil was not characterized for soil type or analyzed for contaminants present.

The growth of fungi from fungal-alginate bead formulations amended with corncob grits was assessed. Six beads of each formulation were placed 0.5 cm deep in a 35 mm petri dish containing 10 g of each sample of collected soil. Soils were incubated at 28° C. and maintained slightly below field capacity for 10 days, after which time the soil was observed for the percentage of beads with hyphal growth on the surface of the bead or soil matrix. The results are shown in Table 4.

The encapsulated formulation of *Aspergillus niger*, (a common soil inhabiting fungus), grew on the surface of the beads but was unable to colonize any of the soil tested. On the other hand, in this experiment, the total viability of *P. chrysosporium* mycelial formulation was lower overall than that of the P. chrysosporium spore formulation, but the former formulation was able to more rapidly colonize the soil matrix. Formulations containing *P. chrysosporium* mycelium demonstrated the most rapid growth, showing slight growth on beads by day two, and extensive growth and soil colonization by day ten. Hyphal mats of this formulation persisted in the soil longer than those of other formulations, and were observed after two months when growth of other formulations had declined. The *P. chrysosporium* spore formulation grew initially on the alginate beads but colonization of the soil was delayed. *M. troyanus* (collected from the old Inger Site) was able to colonize the beads on all soil types, but did not readily colonize the soil substrate. When hyphal growth did extend into the soil substrate surrounding the beads, *M. troyanus* mycelial growth was limited and formed hyphal connections from one bead to the next. In contrast, *P. chrysosporium* was able to colonize the soil surface rapidly and form new colonies where the beads were not located in the soil. This might be expected since *P. chrysosporium* readily forms conidiospores (in culture) while *M. troyanus* does not.

A prophetic example illustrating likely events during colonization of soil by an alginate granule formulation of a sporulating fungus appears at EXAMPLE 7.

EXAMPLE 6

Detection of Fungal Lignin Peroxidase by ELISA

Mycelium of *P. chrysosporium*, *M. troyanus*, and a non-white-rot fungus *Aspergillus niger*, were grown in malt extract broth as previously described. Fungal/alginate beads (25 beads per packet) were placed in non-sterilized Conover AP soil, essentially as described in Example 1. Fungal growth was observed in the soil and samples were prepared for ELISA. Antigen-soil extracts and mycelial extracts were prepared by grinding either 100 $\mu$l of mycelium from a broth culture, or 100 $\mu$l of soil treated with the fungal/alginate formulation, with a sterile mortar and pestle containing 500 $\mu$l of sodium carbonate/sodium bicarbonate coating buffer (pH 9.5). A dilution series of each extract was prepared. A 100 $\mu$l sample of each dilution was incubated in a standard 96-well microliter plate (Titertex, Inc.) according to standard methods. Lignin peroxidase bound to the microliter plate was detected using rabbit anti-lignin peroxidase Ab, followed by goat anti-rabbit Ab conjugated with alkaline phosphatase. Absorbance was measured at 405 nm. Samples were compared with purified lignin peroxidase (Tienzyme, Inc.) as standard.

Figure 2:
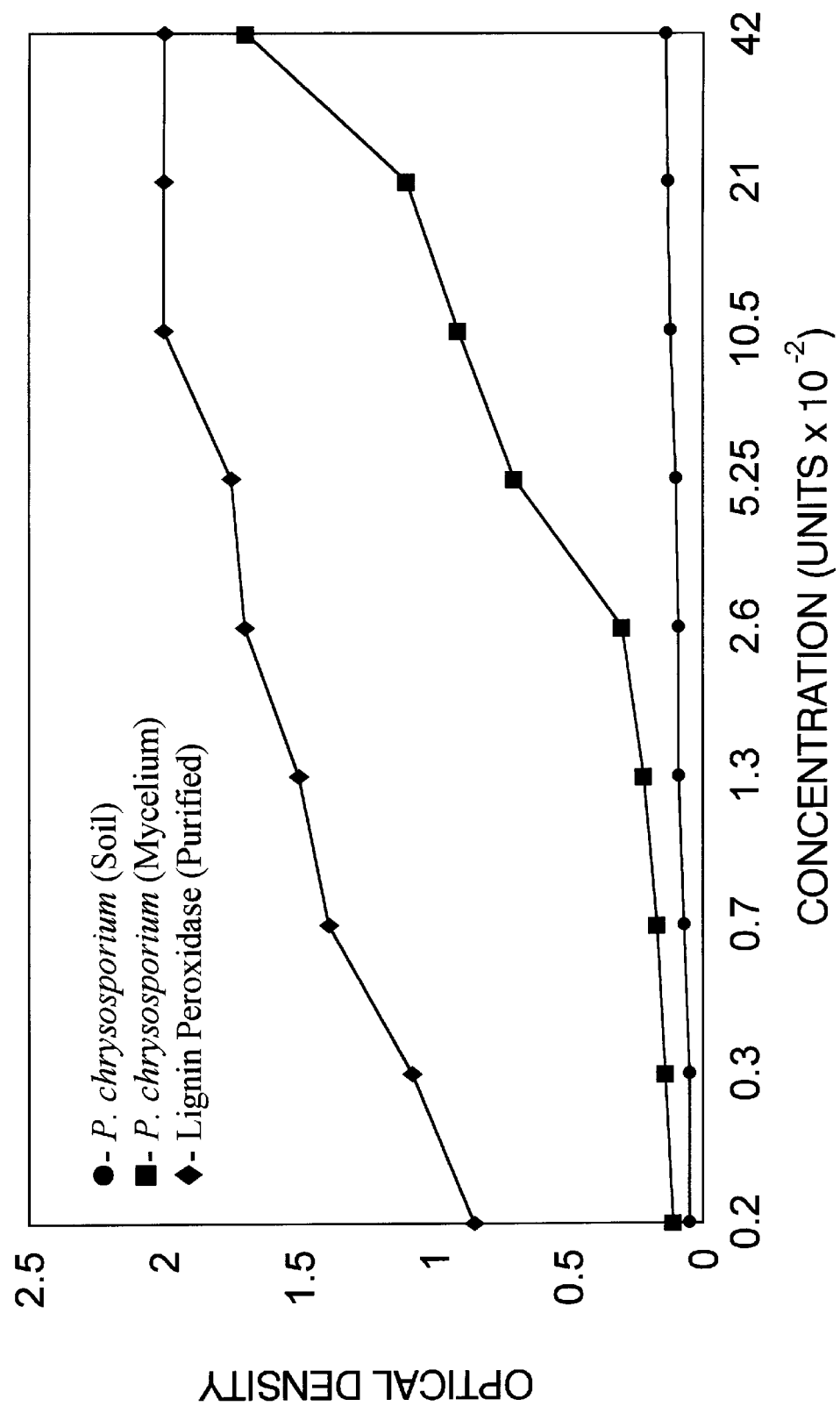

Lignin peroxidase was detected in higher concentrations in *P. chrysosporium* mycelium grown in broth than in soil samples (FIG. 2). This is probably due to a lower hyphal content in the soil per unit weight than in an axenic in vitro culture. The enzyme was not detected in *M. troyanus* myceliur or soil samples (data not shown). It is possible that an alternative pathway, or a ligninase other than lignin peroxidase (such as laccase), may be involved in degradation by this organism. (In a separate experiment, lignin peroxidase was detected in another white rot fungus, *Trametes versicolor*.) However, lignin peroxidase was not detected from either broth cultures of, or soil samples inoculated with, *A. niger*, a common soil fungus which is not known to produce ligninase (data not shown). Lignin peroxidase was not detected in ELISA of soil without the fungal/alginate formulation added. In summary, the delivery of ligninolytic fungi to soil, encapsulated in alginate beads leads to the production of lignin peroxidase in situ.

EXAMPLE 7

The Colonization of Soil by Fungal Inoculum Encapsulated within Alginate Gel Alginate granules containing the inoculum are introduced into the soil. After the granule has absorbed moisture from the soil, the increased water activity level of the alginate gel stimulates the fungal inoculum to grow. Fungal hyphae grow through the gel matrix to the perimeter of the hydrated granule or gel bead and beyond the bead into the soil, and the fungus sporulates at the surface of the gel bead and/or in the surrounding soil. The spores, which may be motile or non-motile, are released and are disseminated, e.g., by water flow or by the movement of vector organisms, to a location more or less distant from the gel bead whence they originated. Disseminated spores germinate to reinitiate vegetative mycelial growth, the hyphae of which spread within the soil. Secondary mycelial growth in turn sporulates and spores are released into, and disseminated further within, the soil. The above series of events, including: a phase of vegetative mycelial growth, followed by sporulation, dissemination of the spores, and germination of the spores to reinitiate vegetative mycelial growth, are repeated a number of times, until the soil is colonized by the fungus.

A working Example of colonization of soil by an alginate granule formulation of a sporulating fungus appears at EXAMPLE 5.

EXAMPLE 8

Degradation of benzo [a]pyrene by *M. troyanus*

Fifty ml aliquots of Sabouraud's dextrose broth in 250 ml Erlenmeyer flasks were inoculated with mycelial plugs of *M. troyanus* strain no. 216-1867, and the cultures were shaken at 250 rpm under ambient air at 25° C. in the dark for a period of 7 days. Mycelium was harvested by filtration through sterile cheesecloth, rinsed with sterile distilled water, and transferred to 250 ml Erlenmeyer flasks containing 50 ml sterile distilled water. Control flasks containing 50 ml sterile distilled water did not receive inoculum. One mg of benzo[a]pyrene was mixed with 50 $\mu$l of dimethyl sulfoxide (DMSO) and the mixture was added to each flask, and incubation was performed under the conditions described above.

On alternate days over a total period of 30 days, cultures were harvested and extracted twice with 300 ml of ethyl acetate/$H_2O$ (5:1, v/v). The ethyl acetate extract of each culture was evaporated to dryness, the residue suspended in 10 ml of acetone, and the suspension filtered preparatory to HPLC analysis.

HPLC analysis was performed on a C-18 reverse phase column, gradient elution with an initial concentration of methanol:$H_2O$, 30:70 (v/v) and a final concentration of methanol:$H_2O$, 100:0 (v/v) at a flow rate of 1 ml/min with detection at 254 nm. Benzo[a]pyrene concentrations were quantified by comparison with an authentic standard, and the amount of benzo[a]pyrene degraded was calculated for each culture/time point. The experiment was performed in quadruplicate and the data were pooled. The percent degradation of benzo[a]pyrene was then plotted over time (refer to FIG. 3). It is apparent that over 80% of the total amount of benzo[a]pyrene present in the *M. troyanus* cultures was degraded within a period of about 2 weeks. Benzo[a]pyrene was not degraded substantially in control flasks (i.e those which did not contain *M. troyanus* inoculum): benzo[a]pyrene was extracted from control flasks at day 0 with an efficiency of about 85% and the amount of benzo[a]pyrene recovered remained at about the same level over the course of the experiment (control data not shown in FIG. 3)

EXAMPLE 9

Inoculum of *M. troyanus* was grown, harvested, and transferred to 50 ml aliquots of sterile distilled water according to Example 8. At time zero each flask received 96.12 nM of $^{14}$C-labelled benzo[a]pyrene (obtained from the National Cancer Institute, Bethesda, Md.) and 1 mg of unlabelled benzo[a]pyrene in 50 $\mu$l of DMSO. Control flasks containing 50 ml of sterile distilled water together with 96.12 nM of $^{14}$C-labelled benzo[a]pyrene and 1 mg of unlabelled benzo [a]pyrene in 50 $\mu$l of DMSO did not receive inoculum. The flasks were equipped with a gas exchange manifold and sealed with Parafilm. Daily, ambient air was flushed through the gas exchange manifold into each flask and the head space gas was passed through a trap containing Ecoscint to remove and trap volatile organic degradation products. Gas from the Ecoscint trap was then passed through a $CO_2$ trap containing Carbo-trap to capture $^4CO_2$ liberated from $^{14}C$ labelled benzo[a]pyrene. The level of radioactivity present in the contents of each trap was determined by liquid scintillation counting (Beckman LS 7000). The level of radioactivity present in the $CO_2$ trap was used to determine the degree of mineralization of $^{14}C$ benzo[a]pyrene. This experiment was performed in triplicate and the data were pooled. The percentage of benzo[a]pyrene mineralized was plotted over time as shown in FIG. 4.

Figure 5B:
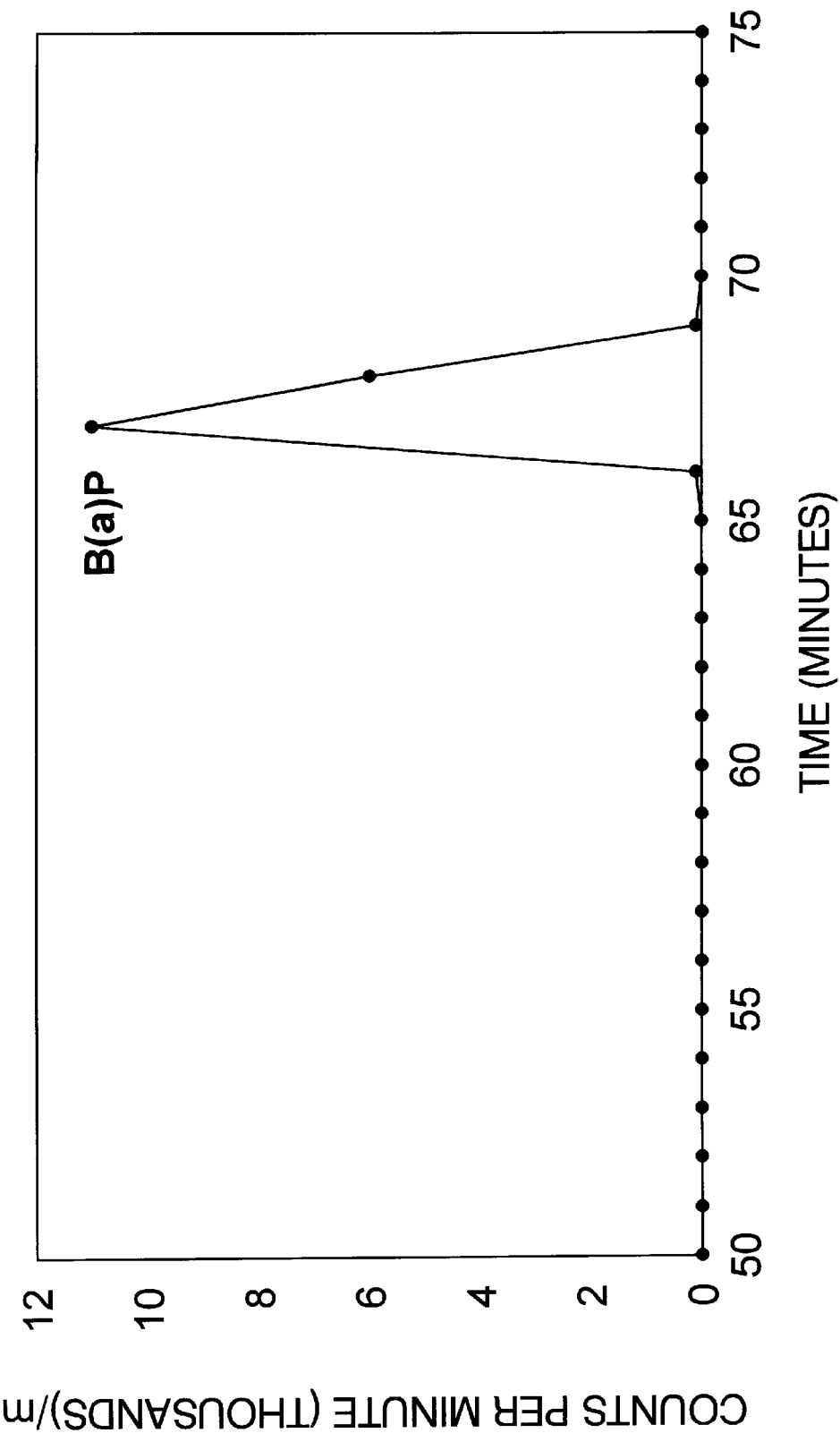

At day 30 a culture was harvested, extracted with ethyl acetate/$H_2O$ according to Example 8 and the extract suspended in acetone for radio-HPLC analysis. At day 30 a control flask which did not receive inoculum was similarly extracted and the extract analyzed by radio-HPLC. The control extract gave a sharp peak corresponding to $^{14}C$ benzo[a]pyrene eluting with a retention time of 67 minutes (FIG. 5B). The *M. troyanus* culture extract gave a much smaller peak with essentially the same retention time (FIG. 5A), indicating that most of the benzo[a]pyrene was degraded to water soluble material. This experiment was performed in triplicate with essentially the same results.

EXAMPLE 10

Flasks containing 50 ml of sterile water, $^{14}C$-labelled benzo[a]pyrene and DMSO, with or without *M. troyanus* inoculum, were provided according to Example 6, and the flasks were incubated under the conditions described above. At day 30, $CO_2$ in the head space of each flask was trapped using Carbo-trap, and the contents of the flasks were extracted with ethyl acetate/$H_2O$ as described above. Levels of radioactivity in the $CO_2$ trap and in the organic and aqueous fractions from each flask were quantified by liquid scintillation counting, and the percentage distribution of total recovered radioactivity was calculated. This experiment was performed in triplicate and the data were pooled. The results are shown in Table 5.

The results demonstrate that *M. troyanus* strain no. 216-1867 has the capacity to mineralize benzo[a]pyrene and to degrade it to water soluble material. In contrast, in the absence of *M. troyanus* the vast majority of mass recovered remains in the form of benzo[a]pyrene.

EXAMPLE 11

The Degradation of benzo[a]pyrene by Fungal Inoculum Formulated a Alginate Beads Alginate bead formulations of *Aspergillus niger*, *Phanerochaete chrysosporium*, and *Marasmiellus troyanus* were cultured for seven days, and the resultant inocula were transferred separately to duplicate Erlenmeyer flasks containing 50 ml of sterile water and of benzo[a]pyrene in DMSO. Two similar flasks containing sterile water and benzo[a]pyrene in DMSO were not inoculated and served as abiotic controls. After incubation for 17 days, the amount of benzo[a]pyrene recovered from each flask was quantified by analytical HPLC, essentially as described above. The percent recovery of benzo[a]pyrene for each treatment was determined, and the results are presented in Table 6. These results demonstrate that inoculum of *M. troyanus* formulated as alginate beads has the ability to degrade benzo[a]pyrene.

Although the invention has been described primarily with reference to formulation of fungi for the purposes of bioremediation, fungi formulated according to the invention may also be used as a convenient form of inoculum for introducing microorganisms into various environments for other purposes, including: composting, and as mushroom spawn. Fungi formulated according to the invention may also be used in drain cleaners and/or for other cleaning purposes, for cleaning grease and other such products. The fungi might even be used as an insect killing agent.

TABLE 1

MICROORGANISMS AND THEIR SOURCE

| Organism No. | Name of Organism | Source of Organism |
|---|---|---|
| 1 | *Phanerochaete chrysosporium* | ATCC, Rockville, MD |
| 2 | *Serratia marcesens* | Inger oil refinery, Darrow, LA |
| 3 | *Cunninghamella echinulata* var. *elegans* | ATCC, Rockville, MD (No. 8688a) |
| 4 | *Marasmiellus troyanus* | Inger oil refinery, Darrow, LA |

TABLE 2

STORAGE TIME AND TEMPERATURE

| | 25 WEEK | | | | 50 WEEK | | | | |
|---|---|---|---|---|---|---|---|---|---|
| Sample formulation | 5° | 25° | 28° | % Total | 5° | 25° | 28° | % Total | Soil Viability |
| *P. chrysosporium* mycelium | | | | | | | | | |
| 1 pyrax clay | 7/10 | 0/10 | 1/10 | 27 | 7/10 | 0/10 | 0/10 | 23 | -- |
| 2 sawdust | 10/10 | 4/10 | 0/10 | 47 | 10/10 | 0/10 | 0/10 | 33 | ++ |
| 3 corncob grits | 10/10 | 1/10 | 2/10 | 43 | 10/10 | 0/10 | 0/10 | 33 | ++ |
| *P chrysosporium* spores | | | | | | | | | |
| 1 pyrax clay | 10/10 | 2/10 | 1/10 | 43 | 8/10 | 0/10 | 1/10 | 30 | -- |
| 2 sawdust | 9/10 | 2/10 | 7/10 | 60 | 10/10 | 0/10 | 0/10 | 33 | -- |
| 3 corncob grits | 10/10 | 7/10 | 8/10 | 83 | 10/10 | 1/10 | 2/10 | 43 | ++ |
| *M. troyanus* mycelium | | | | | | | | | |
| 1 pyrax clay | 0/10 | 0/10 | 0/10 | 0 | -- | -- | -- | -- | -- |
| 2 sawdust | 2/10 | 0/10 | 0/10 | 7 | -- | -- | -- | -- | -- |
| 3 corncob grits | 10/10 | 0/10 | 0/10 | 33 | -- | -- | -- | -- | + |

TABLE 2-continued

| | STORAGE TIME AND TEMPERATURE | | | | | | | | |
|---|---|---|---|---|---|---|---|---|---|
| | 25 WEEK | | | | 50 WEEK | | | | |
| Sample formulation | 5° | 25° | 28° | % Total | 5° | 25° | 28° | % Total | Soil Viability |
| *Aspergillus parasiticus* | | | | | | | | | |
| 1 pyrax clay | 10/10 | 0/10 | 0/10 | 33 | 10/10 | 0/10 | 0/10 | 33 | -- |
| 2 sawdust | 10/10 | 0/10 | 0/10 | 33 | 10/10 | 0/10 | 0/10 | 33 | -- |
| 3 corncob grits | 10/10 | 2/10 | 0/10 | 40 | 0/10 | 0/10 | 0/10 | 33 | -- |
| *Serratia marcesens* | | | | | | | | | |
| 1 pyrax clay | 0/10 | 0/10 | 0/10 | 0 | -- | -- | -- | -- | ND* |
| 2 sawdust | 1/10 | 0/10 | 0/10 | 3 | -- | -- | -- | -- | ND |
| 3 corncob grits | 10/10 | 0/10 | 0/10 | 33 | -- | -- | -- | -- | ND |
| *Cunninghamella elegans* | | | | | | | | | |
| 1 pyrax clay | 0/10 | 0/10 | 0/10 | 0 | -- | -- | -- | -- | ND |
| 2 sawdust | 10/10 | 0/10 | 0/10 | 33 | -- | -- | -- | -- | ND |
| 3 corncob grits | 0/10 | 0/10 | 0/10 | 0 | -- | -- | -- | -- | ND |

Fungal alginate beads containing pyrax clay, sawdust or corncob grits were stored at three temperatures and plated on malt extract media or soil amended with corncob grits, to observe germination and growth.
*ND = not determined.
In the table, -- = no growth, + = slight growth with soil, ++ = extensive growth throughout the soil matrix.
Conover AP (sandy loam, pH 6.6) soil supplemented with corncob grits were used to test soil viability.

TABLE 3

Growth of fungal-alginate beads in soil amended with a carbon nutrient source.

| | SOIL AMENDMENTS | | |
|---|---|---|---|
| FORMULATIONS | CORNCOB GRITS | BAGASSE | SAWDUST |
| ALGINATE BEADS | | | |
| *P. Chrysosporium* mycelium | +++/+[a] | +++/++ | -/- |
| *P. Chrysosporium* spores | +++/++ | +/+ | +/- |
| *Marasmius* mycelium | ++/+ | +/- | -/- |
| MYCELIAL PLUGS | | | |
| *P. Chrysosporium* | -/- | -/- | -/- |
| *M. troyanus* | -/- | -/- | -/- |
| *Aspergillus parasiticus* | -/- | -/- | -/- |
| No fungus/Agar plug | -/- | -/- | -/- |

Seventy g of Conover soil was amended with 5 g of either corncob grits, bagass or sawdust. Twenty-five beads in a wire-mesh screen packet were placed 1.5 cm into the soil jars and held for two months at 32 C., with 60% humidity.
[a]Formulations of alginate beads contained fungi amended with corncob grits. - = no growth, + = growth in bead packet, ++ = growth int soil, +++ = extensive soil colonization.

TABLE 4

Viability of fungal-alginate beads on soil from industrially polluted sites.

| | VIABILITY (%)* DAY | | | | |
|---|---|---|---|---|---|
| FORMULATION | 2 | 4 | 6 | 8 | 10 |
| *P. Chrysosporium* spores SOIL TYPE | | | | | |
| A | 50 | 50 | 50 | 100 | 100 |
| B | 57 | 57 | 50 | 50 | 50 |
| C | ND | ND | ND | ND | ND |
| D | 100 | 100 | 100 | 100 | 100 |
| *P. Chrysosporium* mycelium SOIL TYPE | | | | | |
| A | 50 | 50 | 43 | 33 | 29 |
| B | 100 | 100 | 100 | 100 | 100 |
| C | 100 | 100 | 100 | 100 | 100 |
| D | 50 | 50 | 33 | 25 | 25 |
| *M. troyannus* mycelium SOIL TYPE | | | | | |
| A | 50 | 50 | 50 | 50 | 50 |
| B | 100 | 100 | 100 | 100 | 100 |
| C | 50 | 33 | 50 | 50 | 50 |
| D | 50 | 50 | 100 | 100 | 100 |
| *Aspergillus niger* mycelium SOIL TYPE | | | | | |
| A | 100 | 100 | 100 | 100 | 100 |
| B | 100 | 100 | 100 | 100 | 100 |
| C | ND | ND | ND | ND | ND |
| D | 100 | 100 | 100 | 100 | 100 |

*% of beads showing macroscopically visible hyphal growth.

TABLE 5

Mass balances for benzo(a)pyrene metabolism by *m. troyanus* and abiotic control s in aqueous culture (20 mg/liter) after 30 days.

| CULTURE | % mineralized | % metabolites in water fraction | % extracted in organic fraction | % b(a)P remaining | % mass recovery |
|---|---|---|---|---|---|
| ABIOTIC CONTROL | 0.1 | 1.2 | 85.8 | 85.8 | 87.1 |
| *M. troyanus* | 8.4 | 64.1 | 10.1 | 10.1 | 82.6 |

TABLE 6

Degradation of benzo[a]pyrene in liquid media by fungal strains grown from alginate beads

| Species | Percent recovery benzo[a]pyrene |
|---|---|
| Abiotic control | 104.6 |
| *Aspergillus niger* | 114.3 |
| *Phanerochaete chrysosporium* | 86.1 |
| *Marasmiellus troyanus* | 15.0 |

What is claimed is:

1. A composition for remediating a polluted medium, said composition comprising an inoculum of *Marasmiellus troyanus* strain no. 216-1867, a source of at least one nutrient, and an alginate carrier.

2. A composition for remediating a polluted medium, said composition comprising an inoculum of *Marasmiellus troyanus* strain no. 216-1867 in a non-toxic gel carrier effective for increasing the survivability of said species upon introduction of the species into a contaminated soil; and
   wherein the carrier is further capable of excluding toxic pollutants and of sequestering nutrients to the Marasmiellus species.

* * * * *